(12) United States Patent
Worm

(10) Patent No.: US 8,440,809 B2
(45) Date of Patent: May 14, 2013

(54) RNA ANTAGONISTS TARGETING HSP27

(75) Inventor: Jesper Worm, Copenhagen (DK)

(73) Assignee: Santaris Pharma A/S, Hoersholm (DK)

( * ) Notice: Subject to any disclaimer, the term of this patent is extended or adjusted under 35 U.S.C. 154(b) by 0 days.

(21) Appl. No.: 13/000,278

(22) PCT Filed: Jul. 1, 2009

(86) PCT No.: PCT/IB2009/052860
§ 371 (c)(1),
(2), (4) Date: Jan. 31, 2011

(87) PCT Pub. No.: WO2010/001349
PCT Pub. Date: Jan. 7, 2010

(65) Prior Publication Data
US 2011/0144185 A1    Jun. 16, 2011

Related U.S. Application Data

(60) Provisional application No. 61/077,588, filed on Jul. 2, 2008.

(30) Foreign Application Priority Data

Jul. 2, 2008  (EP) ..................................... 08104612

(51) Int. Cl.
*C07H 21/04* (2006.01)
*C12N 15/11* (2006.01)
*C12Q 1/68* (2006.01)

(52) U.S. Cl.
USPC .......................... 536/24.5; 514/44 A; 435/6.1

(58) Field of Classification Search ........................ None
See application file for complete search history.

(56) References Cited

U.S. PATENT DOCUMENTS

| 7,101,991 B2 | 9/2006 | Gleave et al. |
| 7,250,496 B2 * | 7/2007 | Bentwich ..................... 536/23.1 |
| 2004/0127441 A1 | 7/2004 | Gleave et al. |
| 2005/0113325 A1 * | 5/2005 | Gryaznov et al. ............... 514/44 |

FOREIGN PATENT DOCUMENTS

| WO | 2004030660 | 4/2004 |
| WO | 2007025229 | 3/2007 |
| WO | 2008106781 | 9/2008 |

OTHER PUBLICATIONS

International Search Report issued in PCT/IB2009/052860 and dated Oct. 6, 2009.

* cited by examiner

*Primary Examiner* — Dana Shin
(74) *Attorney, Agent, or Firm* — Fish & Richardson P.C.

(57) ABSTRACT

The present invention relates to oligomer compounds (oligomers), which target Hsp27 mRNA in a cell, leading to reduced expression of Hsp27. Reduction of Hsp27 expression is beneficial for the treatment of certain medical disorders, such as cancer. The invention provides therapeutic compositions comprising oligomers and methods for modulating the expression of Hsp27 using the oligomers, including methods of treatment.

12 Claims, 9 Drawing Sheets

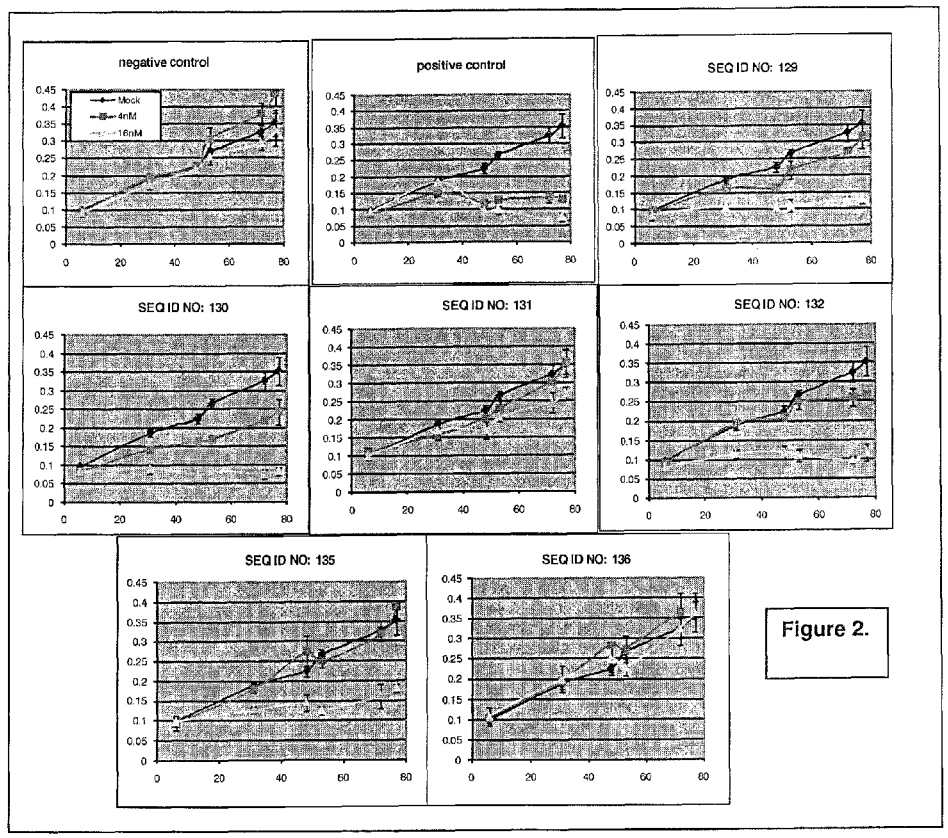

>gi|4996892|ref|NM_001540.2| Homo sapiens heat shock 27kDa protein 1 (HSPB1), mRNA

```
CTCAAACACCGCCTGCTAAAAATACCCGACTGGAGGAGCATAAAAGCGCAGCCGAGCCCAGCGCCCCGCA
CTTTTCTGAGCAGACGTCCAGAGCAGAGTCAGCCAGCATGACCGAGCGCCGCGTCCCCTTCTCGCTCCTG
CGGGGCCCCAGCTGGGACCCCTTCCGCGACTGGTACCCGCATAGCCGCCTCTTCGACCAGGCCTTCGGGC
TGCCCCGGCTGCCGGAGGAGTGGTCGCAGTGGTTAGGCGGCAGCAGCTGGCCAGGCTACGTGCGCCCCT
GCCCCCCGCCGCCATCGAGAGCCCCGCAGTGGCCGCGCCCGCCTACAGCCGCGCGCTCAGCCGGCAACTC
AGCAGCGGGGTCTCGGAGATCCGGCACACTGCGGACCGCTGGCGCGTGTCCCTGGATGTCAACCACTTCG
CCCCGGACGAGCTGACGGTCAAGACCAAGGATGGCGTGGTGGAGATCACCGGCAAGCACGAGGAGCGGCA
GGACGAGCATGGCTACATCTCCCGGTGCTTCACGCGGAAATACACGCTGCCCCCCGGTGTGGACCCCACC
CAAGTTTCCTCCTCCCTGTCCCCTGAGGGCACACTGACCGTGGAGGCCCCCATGCCCAAGCTAGCCACGC
AGTCCAACGAGATCACCATCCCAGTCACCTTCGAGTCGCGGGCCCAGCTTGGGGGCCCAGAAGCTGCAAA
ATCCGATGAGACTGCCGCCAAGTAAAGCCTTAGCCTGGATGCCCACCCCTGCTGCCGCCACTGGCTGTGC
CTCCCCCCGCCACCTGTGTGTTCTTTTGATACATTTATCTTCTGTTTTTCTCAAATAAAGTTCAAAGCAAC
CACCTGTAAAAAAAAAAAAAAAAAAA
```

Figure 10
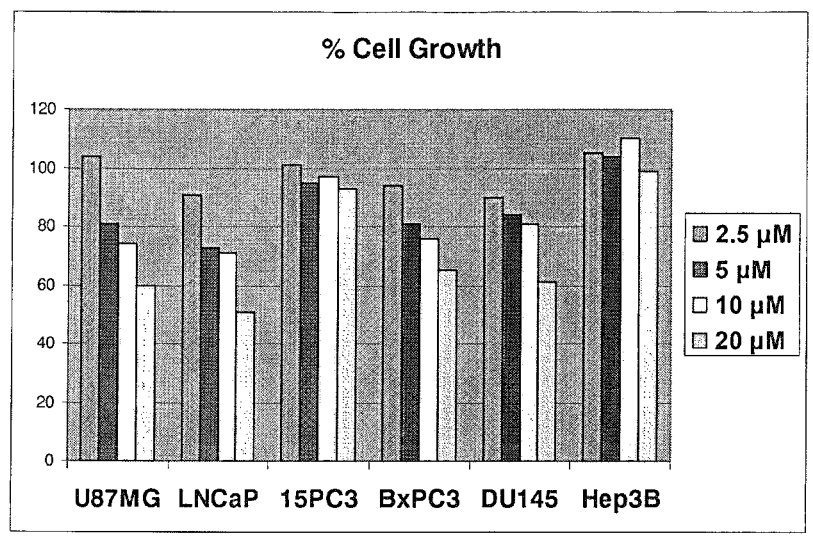
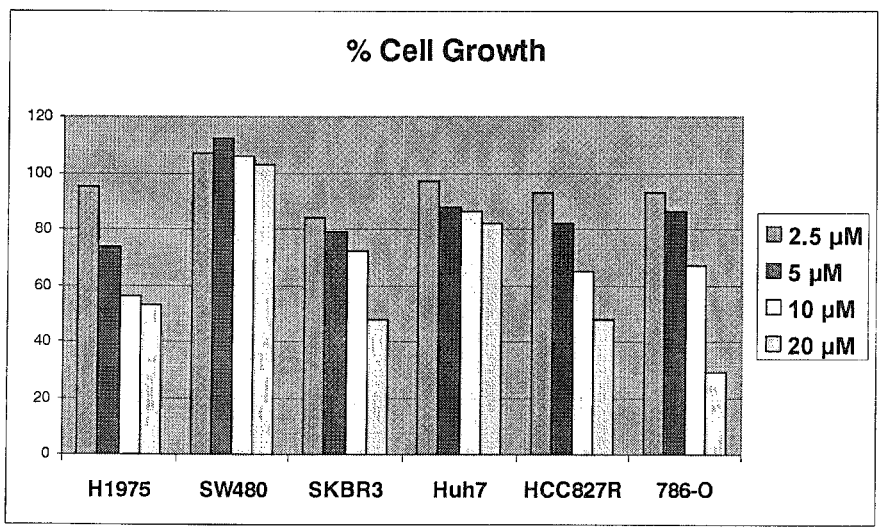

SEQUENCE LISTING

```
<160> NUMBER OF SEQ ID NOS: 145

<210> SEQ ID NO 1
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 1
gagatgtagc catgct                                                      16
```

-continued

```
<210> SEQ ID NO 2
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 2
gagatgtagc catgc                                                     15

<210> SEQ ID NO 3
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 3
agatgtagcc atgct                                                     15

<210> SEQ ID NO 4
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 4
gagatgtagc catg                                                      14

<210> SEQ ID NO 5
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 5
agatgtagcc atgc                                                      14

<210> SEQ ID NO 6
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 6
gatgtagcca tgct                                                      14

<210> SEQ ID NO 7
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 7
gagatgtagc cat                                                       13

<210> SEQ ID NO 8
<211> LENGTH: 13
```

```
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 8
agatgtagcc atg                                                          13

<210> SEQ ID NO 9
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 9
gatgtagcca tgc                                                          13

<210> SEQ ID NO 10
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 10
atgtagccat gct                                                          13

<210> SEQ ID NO 11
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 11
gagatgtagc ca                                                           12

<210> SEQ ID NO 12
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 12
agatgtagcc at                                                           12

<210> SEQ ID NO 13
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 13
gatgtagcca tg                                                           12

<210> SEQ ID NO 14
<211> LENGTH: 12
<212> TYPE: DNA
<213> ORGANISM: artificial
```

```
<220> FEATURE:
<223> OTHER INFORMATION: Oligomer sequence motif - sequence of monomers
      (nucleotides)

<400> SEQUENCE: 14
atgtagccat gc                                                           12

<210> SEQ ID NO 15
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 15
tgtagccatg ct                                                           12

<210> SEQ ID NO 16
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 16
acggtcagtg tgccct                                                       16

<210> SEQ ID NO 17
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 17
acggtcagtg tgccc                                                        15

<210> SEQ ID NO 18
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 18
cggtcagtgt gccct                                                        15

<210> SEQ ID NO 19
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 19
acggtcagtg tgcc                                                         14

<210> SEQ ID NO 20
<211> LENGTH: 14
<212> TYPE: DNA
<213> ORGANISM: artificial
<220> FEATURE:
<223> OTHER INFORMATION: Oligomer sequence motif - sequence of monomers
```

-continued

```
         (nucleotides)

<400> SEQUENCE: 20
cggtcagtgt gccc                                                    14

<210> SEQ ID NO 21
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 21
ggtcagtgtg ccct                                                    14

<210> SEQ ID NO 22
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 22
gtcagtgtgc cct                                                     13

<210> SEQ ID NO 23
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 23
ggtcagtgtg ccc                                                     13

<210> SEQ ID NO 24
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 24
cggtcagtgt gcc                                                     13

<210> SEQ ID NO 25
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 25
acggtcagtg tgc                                                     13

<210> SEQ ID NO 26
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)
```

```
<400> SEQUENCE: 26
acggtcagtg tg                                                           12

<210> SEQ ID NO 27
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 27
cggtcagtgt gc                                                           12

<210> SEQ ID NO 28
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 28
ggtcagtgtg cc                                                           12

<210> SEQ ID NO 29
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 29
gtcagtgtgc cc                                                           12

<210> SEQ ID NO 30
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 30
tcagtgtgcc ct                                                           12

<210> SEQ ID NO 31
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 31
cgtgtatttc cgcgtg                                                       16

<210> SEQ ID NO 32
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 32
```

```
cgtgtatttc cgcgt                                                            15

<210> SEQ ID NO 33
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 33
gtgtatttcc gcgtg                                                            15

<210> SEQ ID NO 34
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 34
cgtgtatttc cgcg                                                             14

<210> SEQ ID NO 35
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 35
gtgtatttcc gcgt                                                             14

<210> SEQ ID NO 36
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 36
tgtatttccg cgtg                                                             14

<210> SEQ ID NO 37
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 37
cgtgtatttc cgc                                                              13

<210> SEQ ID NO 38
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 38
gtgtatttcc gcg                                                              13
```

```
<210> SEQ ID NO 39
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 39
tgtatttccg cgt                                                          13

<210> SEQ ID NO 40
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 40
gtatttccgc gtg                                                          13

<210> SEQ ID NO 41
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 41
cgtgtatttc cg                                                           12

<210> SEQ ID NO 42
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 42
gtgtatttcc gc                                                           12

<210> SEQ ID NO 43
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 43
tgtatttccg cg                                                           12

<210> SEQ ID NO 44
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 44
gtatttccgc gt                                                           12

<210> SEQ ID NO 45
```

-continued

```
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 45
tatttccgcg tg                                                           12

<210> SEQ ID NO 46
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 46
tgcgtggcta gcttgg                                                       16

<210> SEQ ID NO 47
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 47
tgcgtggcta gcttg                                                        15

<210> SEQ ID NO 48
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 48
gcgtggctag cttgg                                                        15

<210> SEQ ID NO 49
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 49
tgcgtggcta gctt                                                         14

<210> SEQ ID NO 50
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 50
gcgtggctag cttg                                                         14

<210> SEQ ID NO 51
<211> LENGTH: 14
<212> TYPE: DNA
```

```
<213> ORGANISM: artificial
<220> FEATURE:
<223> OTHER INFORMATION: Oligomer sequence motif - sequence of monomers
      (nucleotides)

<400> SEQUENCE: 51
cgtggctagc ttgg                                                     14

<210> SEQ ID NO 52
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 52
tgcgtggcta gct                                                      13

<210> SEQ ID NO 53
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 53
gcgtggctag ctt                                                      13

<210> SEQ ID NO 54
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 54
cgtggctagc ttg                                                      13

<210> SEQ ID NO 55
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 55
gtggctagct tgg                                                      13

<210> SEQ ID NO 56
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 56
tgcgtggcta gc                                                       12

<210> SEQ ID NO 57
<211> LENGTH: 12
<212> TYPE: DNA
<213> ORGANISM: artificial
<220> FEATURE:
```

-continued

<223> OTHER INFORMATION: Oligomer sequence motif - sequence of monomers
      (nucleotides)

<400> SEQUENCE: 57
gcgtggctag ct                                                                12

<210> SEQ ID NO 58
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 58
cgtggctagc tt                                                                12

<210> SEQ ID NO 59
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 59
gtggctagct tg                                                                12

<210> SEQ ID NO 60
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 60
tggctagctt gg                                                                12

<210> SEQ ID NO 61
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 61
atggtgatct cgttgg                                                            16

<210> SEQ ID NO 62
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 62
atggtgatct cgttg                                                             15

<210> SEQ ID NO 63
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

```
<400> SEQUENCE: 63
tggtgatctc gttgg                                              15

<210> SEQ ID NO 64
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 64
atggtgatct cgtt                                               14

<210> SEQ ID NO 65
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 65
tggtgatctc gttg                                               14

<210> SEQ ID NO 66
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 66
ggtgatctcg ttgg                                               14

<210> SEQ ID NO 67
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 67
atggtgatct cgt                                                13

<210> SEQ ID NO 68
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 68
tggtgatctc gtt                                                13

<210> SEQ ID NO 69
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 69
```
ggtgatctcg ttg                                                         13

<210> SEQ ID NO 70
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 70
gtgatctcgt tgg                                                         13

<210> SEQ ID NO 71
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 71
atggtgatct cg                                                          12

<210> SEQ ID NO 72
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 72
tggtgatctc gt                                                          12

<210> SEQ ID NO 73
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 73
ggtgatctcg tt                                                          12

<210> SEQ ID NO 74
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 74
gtgatctcgt tg                                                          12

<210> SEQ ID NO 75
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 75
tgatctcgtt gg                                                          12

```
<210> SEQ ID NO 76
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 76
attttgcagc ttctgg                                                    16

<210> SEQ ID NO 77
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 77
attttgcagc ttctg                                                     15

<210> SEQ ID NO 78
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 78
ttttgcagct tctgg                                                     15

<210> SEQ ID NO 79
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 79
attttgcagc ttct                                                      14

<210> SEQ ID NO 80
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 80
ttttgcagct tctg                                                      14

<210> SEQ ID NO 81
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 81
tttgcagctt ctgg                                                      14
```

-continued

```
<210> SEQ ID NO 82
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 82
attttgcagc ttc                                                          13

<210> SEQ ID NO 83
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 83
ttttgcagct tct                                                          13

<210> SEQ ID NO 84
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 84
tttgcagctt ctg                                                          13

<210> SEQ ID NO 85
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 85
ttgcagcttc tgg                                                          13

<210> SEQ ID NO 86
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 86
attttgcagc tt                                                           12

<210> SEQ ID NO 87
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 87
ttttgcagct tc                                                           12

<210> SEQ ID NO 88
<211> LENGTH: 12
```

```
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 88
tttgcagctt ct                                                          12

<210> SEQ ID NO 89
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 89
ttgcagcttc tg                                                          12

<210> SEQ ID NO 90
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 90
tgcagcttct gg                                                          12

<210> SEQ ID NO 91
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 91
ggcacagcca gtggcg                                                      16

<210> SEQ ID NO 92
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 92
ggcacagcca gtggc                                                       15

<210> SEQ ID NO 93
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 93
gcacagccag tggcg                                                       15

<210> SEQ ID NO 94
<211> LENGTH: 14
<212> TYPE: DNA
<213> ORGANISM: artificial
```

```
<220> FEATURE:
<223> OTHER INFORMATION: Oligomer sequence motif - sequence of monomers
      (nucleotides)

<400> SEQUENCE: 94
ggcacagcca gtgg                                                         14

<210> SEQ ID NO 95
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 95
gcacagccag tggc                                                         14

<210> SEQ ID NO 96
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 96
cacagccagt ggcg                                                         14

<210> SEQ ID NO 97
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 97
ggcacagcca gtg                                                          13

<210> SEQ ID NO 98
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 98
gcacagccag tgg                                                          13

<210> SEQ ID NO 99
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 99
cacagccagt ggc                                                          13

<210> SEQ ID NO 100
<211> LENGTH: 13
<212> TYPE: DNA
<213> ORGANISM: artificial
<220> FEATURE:
<223> OTHER INFORMATION: Oligomer sequence motif - sequence of monomers
```

-continued (nucleotides)

<400> SEQUENCE: 100
acagccagtg gcg                                                      13

<210> SEQ ID NO 101
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 101
ggcacagcca gt                                                       12

<210> SEQ ID NO 102
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 102
gcacagccag tg                                                       12

<210> SEQ ID NO 103
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 103
cacagccagt gg                                                       12

<210> SEQ ID NO 104
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 104
acagccagtg gc                                                       12

<210> SEQ ID NO 105
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 105
cagccagtgg cg                                                       12

<210> SEQ ID NO 106
<211> LENGTH: 16
<212> TYPE: DNA
<213> ORGANISM: artificial
<220> FEATURE:
<223> OTHER INFORMATION: Oligomer sequence motif - sequence of monomers
      (nucleotides)

```
<400> SEQUENCE: 106
tatcaaaaga acacac                                                    16

<210> SEQ ID NO 107
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 107
tatcaaaaga acaca                                                     15

<210> SEQ ID NO 108
<211> LENGTH: 15
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 108
atcaaaagaa cacac                                                     15

<210> SEQ ID NO 109
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 109
tatcaaaaga acac                                                      14

<210> SEQ ID NO 110
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 110
atcaaaagaa caca                                                      14

<210> SEQ ID NO 111
<211> LENGTH: 14
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 111
tcaaaagaac acac                                                      14

<210> SEQ ID NO 112
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 112
```
tatcaaaaga aca                                                        13

<210> SEQ ID NO 113
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 113
atcaaaagaa cac                                                        13

<210> SEQ ID NO 114
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 114
tcaaaagaac aca                                                        13

<210> SEQ ID NO 115
<211> LENGTH: 13
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 115
caaaagaaca cac                                                        13

<210> SEQ ID NO 116
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 116
tatcaaaaga ac                                                         12

<210> SEQ ID NO 117
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 117
atcaaaagaa ca                                                         12

<210> SEQ ID NO 118
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 118
tcaaaagaac ac                                                         12

```
<210> SEQ ID NO 119
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 119
caaaagaaca ca                                                             12

<210> SEQ ID NO 120
<211> LENGTH: 12
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 120
aaaagaacac ac                                                             12

<210> SEQ ID NO 121
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 121
ccgggagatg tagccatgct cgtc                                                24

<210> SEQ ID NO 122
<211> LENGTH: 25
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 122
ctccacggtg cagtgtgccc tcagg                                               25

<210> SEQ ID NO 123
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 123
gcagcgtgta tttccgcgtg aagc                                                24

<210> SEQ ID NO 124
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 124
ggactgcgtg gctagcttgg gcat                                                24

<210> SEQ ID NO 125
```

```
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 125
tgggatggtg atctcgttgg actg                                              24

<210> SEQ ID NO 126
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 126
tcggattttg cagcttctgg gccc                                              24

<210> SEQ ID NO 127
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 127
gggaggcaca gccagtggcg gcag                                              24

<210> SEQ ID NO 128
<211> LENGTH: 24
<212> TYPE: DNA
<213> ORGANISM: artificial
<220> FEATURE:
<223> OTHER INFORMATION: Oligomer sequence motif - sequence of monomers
      (nucleotides)

<400> SEQUENCE: 128
aatgtatcaa aagaacacac aggt                                              24

<210> SEQ ID NO 129
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 129
gagatgtagc catgct                                                       16

<210> SEQ ID NO 130
<211> LENGTH: 16
```

```
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 130
acggtcagtg tgccct                                                  16

<210> SEQ ID NO 131
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 131
cgtgtatttc cgcgtg                                                  16

<210> SEQ ID NO 132
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 132
tgcgtggcta gcttgg                                                  16

<210> SEQ ID NO 133
```

```
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 133
atggtgatct cgttgg                                                         16

<210> SEQ ID NO 134
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 134
attttgcagc ttctgg                                                         16

<210> SEQ ID NO 135
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 135
ggcacagcca gtggcg                                                         16
```

```
<210> SEQ ID NO 136
<211> LENGTH: 16
<212> TYPE: DNA
<213> ORGANISM: artificial
<220> FEATURE:
<223> OTHER INFORMATION: Oligomer design or LNA oligomer compound
<220> FEATURE:
<221> NAME/KEY: misc_feature
<222> LOCATION: (1)..(16)
<223> OTHER INFORMATION: Internucleoside linkage, preferably
      phosphorothioate linkage
<220> FEATURE:
<221> NAME/KEY: misc_feature
<222> LOCATION: (1)..(3)
<223> OTHER INFORMATION: Nucleotide analogue, such as LNA, such as
      beta-D-oxy LNA
<220> FEATURE:
<221> NAME/KEY: misc_feature
<222> LOCATION: (14)..(16)
<223> OTHER INFORMATION: Nucleotide analogue, such as LNA, such as
      beta-D-oxy LNA

<400> SEQUENCE: 136
tatcaaaaga acacac                                                       16

<210> SEQ ID NO 137
<211> LENGTH: 865
<212> TYPE: DNA
<213> ORGANISM: homo sapiens

<400> SEQUENCE: 137
ctcaaacacc gcctgctaaa aatacccgac tggaggagca taaaagcgca gccgagccca       60
gcgccccgca cttttctgag cagacgtcca gagcagagtc agccagcatg accgagcgcc      120
gcgtcccctt ctcgctcctg cggggcccca gctgggaccc cttccgcgac tggtacccgc      180
atagccgcct cttcgaccag gccttcgggc tgccccggct gccggaggag tggtcgcagt      240
ggttaggcgg cagcagctgg ccaggctacg tgccgccccct gccccccgcc gccatcgaga      300
gccccgcagt ggccgcgccc gcctacagcc gcgcgctcag ccggcaactc agcagcgggg      360
tctcggagat ccggcacact gcggaccgct ggcgcgtgtc cctggatgtc aaccacttcg      420
ccccggacga gctgacggtc aagaccaagg atggcgtggt ggagatcacc ggcaagcacg      480
aggagcggca ggacgagcat ggctacatct cccggtgctt cacgcggaaa tacacgctgc      540
cccccggtgt ggaccccacc caagtttcct cctccctgtc ccctgagggc acactgaccg      600
tggaggcccc catgcccaag ctagccacgc agtccaacga gatcaccatc ccagtcacct      660
tcgagtcgcg ggcccagctt gggggcccag aagctgcaaa atccgatgag actgccgcca      720
agtaaagcct tagcctggat gcccaccct gctgccgcca ctggctgtgc ctcccccgcc      780
acctgtgtgt tcttttgata catttatctt ctgttttcct caaataaagt tcaaagcaac      840
cacctgtaaa aaaaaaaaaa aaaaa                                            865

<210> SEQ ID NO 138
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
```

```
<220> FEATURE:
<221> NAME/KEY: misc_feature
<222> LOCATION: (14)..(16)
<223> OTHER INFORMATION: Beta-D-oxy LNA, all LNA cytosines 5methyl
      cytosine

<400> SEQUENCE: 138
gagatgtagc catgct                                                      16

<210> SEQ ID NO 139
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
<222> LOCATION: (14)..(16)
<223> OTHER INFORMATION: Beta-D-oxy LNA, all LNA cytosines 5methyl
      cytosine

<400> SEQUENCE: 139
acggtcagtg tgccct                                                      16

<210> SEQ ID NO 140
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
<222> LOCATION: (14)..(16)
<223> OTHER INFORMATION: Beta-D-oxy LNA, all LNA cytosines 5methyl
      cytosine

<400> SEQUENCE: 140
cgtgtatttc cgcgtg                                                      16

<210> SEQ ID NO 141
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
```

```
<222> LOCATION: (14)..(16)
<223> OTHER INFORMATION: Beta-D-oxy LNA, all LNA cytosines 5methyl
      cytosine

<400> SEQUENCE: 141
tgcgtggcta gcttgg                                                    16

<210> SEQ ID NO 142
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
<222> LOCATION: (14)..(16)
<223> OTHER INFORMATION: Beta-D-oxy LNA, all LNA cytosines 5methyl
      cytosine

<400> SEQUENCE: 142
atggtgatct cgttgg                                                    16

<210> SEQ ID NO 143
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
<222> LOCATION: (14)..(16)
<223> OTHER INFORMATION: Beta-D-oxy LNA, all LNA cytosines 5methyl
      cytosine

<400> SEQUENCE: 143
attttgcagc ttctgg                                                    16

<210> SEQ ID NO 144
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
<222> LOCATION: (14)..(16)
<223> OTHER INFORMATION: Beta-D-oxy LNA, all LNA cytosines 5methyl
```

```
              cytosine

<400> SEQUENCE: 144
ggcacagcca gtggcg                                                   16

<210> SEQ ID NO 145
<211> LENGTH: 16
<212> TYPE: DNA
<213> ORGANISM: artificial
<220> FEATURE:
<223> OTHER INFORMATION: LNA oligomer compound
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: Beta-D-oxy LNA, all LNA cytosines 5methyl
      cytosine
<220> FEATURE:
<221> NAME/KEY: misc_feature
<222> LOCATION: (14)..(16)
<223> OTHER INFORMATION: Beta-D-oxy LNA, all LNA cytosines 5methyl
      cytosine

<400> SEQUENCE: 145
tatcaaaaga acacac                                                   16
```

RNA ANTAGONISTS TARGETING HSP27

RELATED CASES

This application is the national stage of International Application No. PCT/IB2009/052860 filed Jul. 1, 2009, which claims the benefit of priority U.S. Provisional Application Ser. No. 61/077,588 filed 2 Jul. 2008 and from EP 08104612 filed on 2 Jul. 2008, the contents of each of which are incorporated herein by reference.

FIELD OF INVENTION

The invention provides compounds, compositions and methods for modulating the expression of Hsp27. In particular, this invention relates to oligomeric compounds (oligomers), which target Hsp27 mRNA in a cell, leading to reduced expression of Hsp27. Reduction of Hsp27 expression is beneficial for a range of medical disorders, such as cancer.

BACKGROUND

Hsp27 is a molecular chaperone that is constitutively expressed in several mammalian cells, but particularly in pathological conditions. In addition, these proteins share anti-apoptotic properties and are tumorigenic when expressed in cancer cells. Hsp27 expression is associated with a poor prognosis in virtually all cancer forms such as leukemias, breast, gastric, liver, and prostate cancer, and osteosarcomas. Increased Hsp27 expression may also predict the response to some anticancer treatments. For example, expression of Hsp27 is implicated in resistance to chemotherapy in breast cancer and predicts a poor response to chemotherapy in leukemia patients.

Besides cancer modulation, the expression of Hsp27 proteins have also been considered to be of importance for treatment of myopathies and asthma.

Oncogenex are developing an antisense oligonucleotide which targets the Hsp27 mRNA—referred to as the OGX-427 antisense compound. WO2007/025229 and U.S. Pat. No. 7,101,991 disclose antisense oligonucleotides which target Hsp27.

There is a need for improved antisense oligomers targeting Hsp27.

SUMMARY OF INVENTION

The invention provides an oligomer of from 10-50 monomers, such as 10-30 monomers, which comprises a contiguous sequence (a first region) of 10-50 monomers, such as 10-30 monomers, wherein the contiguous sequence (the first region) is at least 80% (e.g., 85%, 90%, 95%, 98%, or 99%) identical (homologous) to a region corresponding to a mammalian Hsp27 gene or mRNA or to the reverse complement of a target region of a nucleic acid which encodes a mammalian Hsp27, such as a mammalian Hsp27 gene or mRNA, such as a nucleic acid having the sequence set forth in SEQ ID NO: 137, or naturally occurring variants thereof. Thus, for example, the oligomer hybridizes to a region of a single-stranded nucleic acid molecule having the sequence shown in SEQ ID NO: 137.

The invention provides an oligomer of from 10-50 monomers, such as 10-30 monomers, which comprises a contiguous sequence (a first region) of 10-50 monomers, such as 10-30 monomers, wherein the contiguous sequence (the first region) is at least 80% (e.g., 85%, 90%, 95%, 98%, or 99%) identical (homologous) to a region corresponding to a mammalian Hsp27 gene or mRNA, or to the reverse complement of a target region of a nucleic acid which encodes a mammalian Hsp27, such as a mammalian Hsp27 gene or mRNA, such as a nucleic acid having the sequence set forth in SEQ ID NO: 137, or naturally occurring variants thereof; and wherein at least one monomer in the first region is a nucleoside analogue wherein the nucleoside analogue is a Locked Nucleic Acid (LNA) monomer. Thus, for example, the oligomer hybridizes to a region of a single-stranded nucleic acid molecule having the sequence shown in SEQ ID NO: 137.

The invention provides for a conjugate comprising the oligomer according to the invention, and at least one non-nucleotide or non-polynucleotide moiety covalently attached to the oligomer.

The invention provides for a pharmaceutical composition comprising the oligomer or the conjugate according to the invention, and a pharmaceutically acceptable diluent, carrier, salt or adjuvant.

The invention provides for the oligomer or the conjugate according to the invention, for use as a medicament, such as for the treatment of a disease or a medical disorder as disclosed herein, such as a hyperproliferative disorder, such as cancer or other hyperproliferative disorder.

The invention provides for the use of an oligomer or the conjugate according to the invention, for the manufacture of a medicament for the treatment of a disease or disorder as disclosed herein, such as a hyperproliferative disorder, such as cancer.

The invention provides for a method of treating a disease or disorder as disclosed herein, such as a hyperproliferative disorder, such as cancer, the method comprising administering, e.g. an effective amount of, an oligomer, a conjugate or a pharmaceutical composition according to the invention to an animal suffering from or susceptible to the disease or disorder (such as a patient suffering from or susceptible to the disease or disorder).

In one embodiment, the disease or disorder or condition is associated with overexpression of a Hsp27 gene or mRNA.

The invention provides for a method for the inhibition of Hsp27 in a cell which is expressing Hsp27, the method comprising contacting the cell with an oligomer, or a conjugate according to the invention so as to affect the inhibition of Hsp27 expression (e.g. to cause an inhibitory effect on Hsp27 expression) in said cell.

The invention provides an oligomer of from 10-50 monomers, which comprises a first region of 10-50 contiguous monomers, wherein the sequence of the first region is at least 80% identical to a region corresponding to a mammalian Hsp27 gene or to the reverse complement of a target region of a nucleic acid which encodes a mammalian Hsp27.

The invention further provides a conjugate comprising the oligomer according to the invention, which comprises at least one non-nucleotide or non-polynucleotide moiety ("conjugated moiety") covalently attached to the oligomer of the invention.

The invention provides for pharmaceutical compositions comprising an oligomer or conjugate of the invention, and a pharmaceutically acceptable diluent, carrier, salt or adjuvant.

The invention further provides for an oligomer according to the invention, for use in medicine.

The invention further provides for the use of the oligomer of the invention for the manufacture of a medicament for the treatment of one or more of the diseases referred to herein, such as a disease selected from the group consisting of cancer, myopathies and asthma.

The invention further provides for an oligomer according to the invention, for use for the treatment of one or more of the diseases referred to herein, such as a disease selected from the group consisting of cancer, myopathies and asthma.

Pharmaceutical and other compositions comprising an oligomer of the invention are also provided. Further provided are methods of down-regulating the expression of Hsp27 in cells or tissues comprising contacting said cells or tissues, in vitro or in vivo, with an effective amount of one or more of the oligomers, conjugates or compositions of the invention.

Also disclosed are methods of treating an animal (a non-human animal or a human) suspected of having, or susceptible to, a disease or condition, associated with expression, or over-expression of Hsp27 by administering to the non-human animal or human a therapeutically or prophylactically effective amount of one or more of the oligomers, conjugates or pharmaceutical compositions of the invention. Further, methods of using oligomers for the inhibition of expression of Hsp27, and for treatment of diseases associated with activity of Hsp27 are provided.

The invention provides for a method for treating a disease selected from the group consisting of: cancer, myopathies and asthma, the method comprising administering an effective amount of one or more oligomers, conjugates, or pharmaceutical compositions thereof to an animal in need thereof (such as a patient in need thereof).

The invention provides for methods of inhibiting (e.g., by down-regulating) the expression of Hsp27 in a cell or a tissue, the method comprising the step of contacting the cell or tissue, in vitro or in vivo, with an effective amount of one or more oligomers, conjugates, or pharmaceutical compositions thereof, to effect down-regulation of expression of Hsp27.

BRIEF DESCRIPTION OF FIGURES

FIG. 2. MTS cell proliferation after transfection of PC3 cells with the indicated oligonucleotides FIG. 3. Hsp27 cDNA (mRNA) sequence—human—SEQ ID NO 137. GenBank accession number NM_001540.

FIG. 10. Long-term culture with the oligomer having the sequence set forth in SEQ ID NO: 135.

DETAILED DESCRIPTION OF INVENTION

The Oligomer

Figure 1:
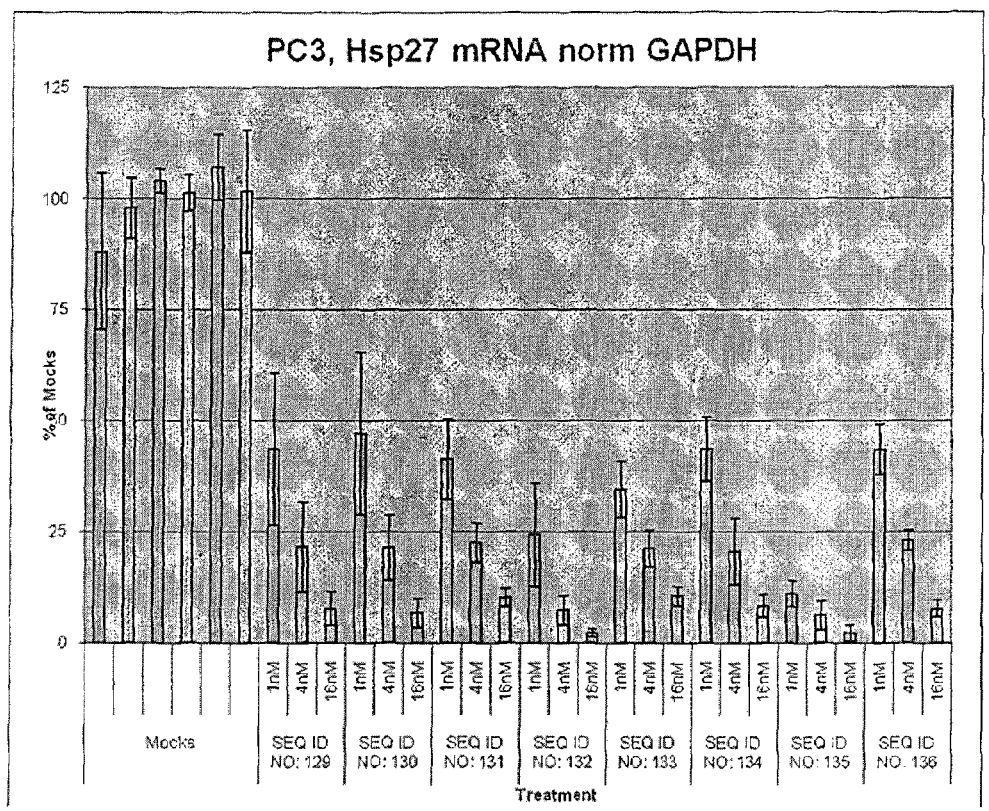
FIG. 1. Real-time Quantitative PCR showing Hsp27 mRNA normalized to GAPDH, 24 h after transfection of PC3 cells with the indicated oligonucleotides.

The invention employs oligomeric compounds (referred herein as oligomers), for use in modulating the function of nucleic acid molecules encoding mammalian Hsp27, such as the Hsp27 nucleic acid shown in SEQ ID NO: 137, and naturally occurring variants of such nucleic acid molecules encoding mammalian Hsp27. The term "oligomer" in the context of the invention, refers to a molecule formed by covalent linkage of two or more monomers (i.e. an oligonucleotide). In some embodiments, the oligomer comprises or consists of from 10-50 covalently linked monomers, such as from 10-30 covalently linked monomers, such as 10-24 covalently linked monomers, such as 10-18 covalently linked monomers, such as 10-16 covalently linked monomers.

In some embodiments, the terms "nucleoside", "nucleotide", "unit" and "monomer" are used interchangeably. It will be recognised that when referring to a sequence of nucleotides or monomers, what is referred to is the sequence of bases, such as A, T, G, C or U.

The term "nucleotide" as used herein, refers to a glycoside comprising a sugar moiety, a base moiety and a covalently linked group (linkage group) such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In the field of biochemistry, the term "nucleoside" is commonly used to refer to a glycoside comprising a sugar moiety and a base moiety, and may therefore be used when referring to the "nucleotide" units, which are covalently linked by the internucleotide linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refers to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

The person having ordinary skill in the art would understand that, in the context of the present invention, the 5' terminal nucleotide of an oligonucleotide (oligomer) does not comprise a 5' internucleotide linkage group, although it may or may not comprise a 5' terminal group.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified nucleobase (base) moiety (i.e., the purine and pyrimidine heterocycles adenine, guanine, cytosine, thymine or uracil) and "nucleoside analogues," which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer," "locked monomer," or "LNA monomer" is a nucleoside analogue having a bicyclic sugar, as further described herein below.

The terms "corresponding to" and "corresponds to" refer to the comparison between the nucleotide/nucleoside sequence (i.e. the nucleobase or base sequence) of the oligomer or contiguous nucleotide/nucleoside sequence (a first region) and the equivalent contiguous nucleotide/nucleoside sequence of a further sequence selected from either i) a subsequence of the reverse complement of the nucleic acid target, and/or ii) the sequence of nucleotides/nucleosides provided herein. Nucleotide/nucleoside analogues are compared directly to their equivalent or corresponding nucleotides/nucleosides. A first region which corresponds to a further sequence under i) or ii) typically is identical to that sequence over the length of the first region (such as the contiguous nucleotide/nucleoside sequence) or, as described herein may, in some embodiments, be at least 80% homologous to a corresponding sequence, such as at least 85%, at least 90%, at least 91%, at least 92%, at least 93%, at least 94%, at least 95%, at least 96% homologous, at least 97% homologous, at least 98% homologous, at least 99% homologous, such as 100% homologous (identical).

The terms "corresponding nucleoside analogue" and "corresponding nucleoside" indicate that the base moiety in the nucleoside analogue and the base moiety in the nucleoside are identical. For example, when the "nucleoside" contains a 2'-deoxyribose sugar linked to an adenine, the "corresponding nucleoside analogue" contains, for example, a modified sugar linked to an adenine base moiety.

The terms "oligomer", "oligomeric compound" and "oligonucleotide" are used interchangeably in the context of the invention, and refer to a molecule formed by covalent linkage of two or more monomers by, for example, a phosphate group (forming a phosphodiester linkage between nucleosides) or a phosphorothioate group (forming a phosphorothioate linkage between nucleosides). The oligomer consists of, or comprises, 10-50 monomers, such as 10-30 monomers, such as 10-24 monomers, such as 10-18 monomers, such as 10-16 monomers. The oligomer consists of or comprises a first region (a contiguous sequence) which, for example, consists of 9-30 contiguous monomers, such as 9-24 monomers, such as 9-18 monomers, such as 9-16 monomers.

In some embodiments, the terms "contiguous sequence", "contiguous monomers" and "region" are interchangeable.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases and high affinity and specificity for the nucleic acid target. LNA monomers are particularly preferred, for example, for conferring one or more of the above-mentioned properties.

In various embodiments, one or more nucleoside analogues present within the oligomer are "silent" or "equivalent" in function to the corresponding natural nucleoside, i.e., have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example, by producing increased binding affinity to the target region of the target nucleic acid and/or increased resistance to nucleases, such as intracellular nucleases, and/or increased ease of transport into the cell.

Thus, in various embodiments, oligomers according to the invention comprise nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the oligomers of the invention, the term "at least one" includes the terms "at least two" and "at least three" and "at least four." Likewise, in some embodiments, the term "at least two" comprises the terms "at least three" and "at least four."

In some embodiments, the oligomer comprises or consists of 9, 10, 11, 12, 13, 14, 15, 16, 17, 18, 19, 20, 21, 22, 23, 24, 25, 26, 27, 28, 29 or 30 contiguous monomers in the first region.

In some embodiments, the oligomer comprises or consists of 10-24 contiguous monomers, such as 10-22 contiguous monomers, such as 10-18 contiguous monomers, such as 10-16 contiguous monomers, such as 12-18 contiguous monomers, such as 13-17 or 12-16 contiguous monomers, such as 13, 14, 15, 16 or 24 contiguous monomers. It should be understood that when a range is given for an oligomer, or contiguous nucleotide sequence length it includes the lower and upper lengths provided in the range, for example from (or between) 10-30, includes both 10 and 30.

In certain embodiments, the oligomer comprises or consists of 10, 11, 12, 13, or 14 contiguous monomers.

In various embodiments, the oligomer according to the invention consists of no more than 24 monomers, such as no more than 22 monomers, such as no more than 20 monomers, such as no more than 18 monomers, such as 15, 16 or 17 monomers. In some embodiments, the oligomer of the invention comprises less than 20 monomers.

In various embodiments, the oligomers of the invention do not comprise RNA monomers.

In various embodiments, the oligomers according to the invention are linear molecules or are linear as synthesised. The oligomer, in such embodiments, is a single stranded molecule, and typically does not comprise short regions of, for example, at least 3, 4 or 5 contiguous monomers, which are complementary to another region within the same oligomer such that the oligomer forms an internal duplex. In some embodiments, the oligomer is essentially not double stranded, i.e., is not a siRNA.

In some embodiments, the oligomer of the invention consists of a contiguous stretch of monomers (a first region), the sequence of which is identified by a SEQ ID NO disclosed herein (see, e.g., Tables 1-3). In other embodiments, the oligomer comprises a first region, the region consisting of a contiguous stretch of monomers of the nucleic acid molecule encoding the target, and one or more additional regions which consist of at least one additional monomer. In some embodiments, the sequence of the first region is identified by a SEQ ID NO disclosed herein.

Gapmer Design

Typically, the oligomer of the invention is a gapmer.

A "gapmer" is an oligomer which comprises a contiguous stretch of monomers capable of recruiting an RNAse (e.g., such as RNAseH) as further described herein below, such as a region of at least 6 or 7 DNA monomers, referred to herein as region B. Region B is flanked both on its 5' and 3' ends by regions respectively referred to as regions A and C, each of regions A and C comprising or consisting of nucleoside analogues, such as affinity-enhancing nucleoside analoagues, such as 1-6 nucleoside analogues. The RNase is preferably RNaseH, such as E. coli or human RNaseH. The capability of an oligomer to recruit RNaseH is determined when the oligomer is formed in a duplex with a complementary RNA molecule (such as a mRNA target).

In some embodiments, the monomers which are capable of recruiting RNAse are selected from the group consisting of DNA monomers, alpha-L-LNA monomers, C4' alkylated DNA monomers (see PCT/EP2009/050349 and Vester et al., Bioorg. Med. Chem. Lett. 18 (2008) 2296-2300, hereby incorporated by reference), and UNA (unlocked nucleic acid) nucleotides (see Fluiter et al., Mol. Biosyst., 2009, 10, 1039 hereby incorporated by reference). UNA is unlocked nucleic acid, typically where the C2'-C3' bond (i.e. the covalent carbon-carbon bond between the C2' and C3' carbons) of the sugar has been removed, forming an unlocked "sugar" residue.

Typically, the gapmer comprises regions, from 5' to 3', A-B-C, or optionally A-B-C-D or D-A-B-C, wherein: region A (A) consists of or comprises at least one nucleoside analogue, such as at least one LNA monomer, such as 1-6 nucleoside analogues, such as LNA monomers, and region B (B) consists of or comprises at least five contiguous monomers which are capable of recruiting RNAse (when formed in a duplex with a complementary target region of the target RNA molecule, such as the mRNA target), such as DNA monomers; region C (C) consists of or comprises at least one nucleoside analogue, such as at least one LNA monomer, such as 1-6 nucleoside analogues, such as LNA monomers; and region D (D), when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers (e.g. consecutive nucleotides) which are capable of recruiting RNAse, such as RNaseH, or 6-10, or 7-9 contiguous monomers, such as 10 or 9 or 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In various embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 monomers, such as DNA monomers.

Further gapmer designs are disclosed in WO2004/046160, which is hereby incorporated by reference.

WO2008/113832, which claims priority from U.S. provisional application 60/977,409 hereby incorporated by reference, refers to 'shortmer' gapmer oligomers. In some embodiments, oligomers presented here may be such shortmer gapmers.

In certain embodiments, the oligomer consists of 10, 11, 12, 13, 14, 15 or 16 monomers, wherein the regions of the oligomer have the pattern (5'-3'), A-B-C, or optionally A-B-C-D or D-A-B-C, wherein: region A consists of 1, 2 or 3 nucleoside analogue monomers, such as LNA monomers; region B consists of 7, 8, 9 or 10 contiguous monomers which are capable of recruiting RNAse, such as RNAseH; and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers. In certain embodiments, region B consists of 8 nucleoside monomers. In certain embodiments, region B consists of 9 nucleoside monomers. In certain embodiments, region B consists of 10 nucleoside monomers. In certain embodiments, region B comprises 1-10 DNA monomers, such as 2, 3, 4, 5, 6, 7, 8 or 9 DNA monomers. In certain embodiments, region B comprises 1-9 DNA monomers, such as 2, 3, 4, 5, 6, 7 or 8 DNA monomers. In certain embodiments, region B consists of DNA monomers. In certain embodiments, region B comprises at least one LNA monomer which is in the alpha-L configuration, such as 2, 3, 4, 5, 6, 7, 8, 9 or 10 LNA monomers in the alpha-L-configuration. In certain embodiments, region B comprises at least one alpha-L-oxy LNA monomer. In certain embodiments, all the LNA monomers in region B that are in the alpha-L-configuration are alpha-L-oxy LNA units. In certain embodiments, the number of monomers present in the A-B-C regions are selected from the group consisting of (nucleoside analogue monomers—region B—nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 3-9-3, 4-9-1, 1-9-4, or; 1-10-1, 1-10-2, 2-10-1, 2-10-2, 1-10-3, 3-10-1, 2-10-3, 3-10-2, or 3-10-3. In certain embodiments, the number of monomers present in the A-B-C regions of the oligomer of the invention respectively is selected from the group consisting of: 2-7-1, 1-7-2, 2-7-2, 3-7-3, 2-7-3, 3-7-2, 3-7-4, and 4-7-3. In certain embodiments, each of regions A and C consists of three LNA monomers, and region B consists of 8 or 9 or 10 nucleoside monomers, preferably DNA monomers. In certain embodiments, each of regions A and C consists of two LNA monomers, and region B consists of 8 or 9 nucleoside monomers, preferably DNA monomers.

In various embodiments, other gapmer designs include those where regions A and/or C consists of 3, 4, 5 or 6 nucleoside analogues, such as monomers containing a 2'-O-methoxyethyl-ribose sugar (2'-MOE) or monomers containing a 2'-fluoro-deoxyribose sugar, and region B consists of 8, 9, 10, 11 or 12 nucleosides, such as DNA monomers, where regions A-B-C have 3-9-3, 3-10-3, 5-10-5 or 4-12-4 monomers. Further gapmer designs are disclosed in WO 2007/146511A2, hereby incorporated by reference.

Internucleoside Linkages

The monomers of the oligomers described herein are coupled together via linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" and "internucleoside linkage" mean a group capable of covalently coupling together two contiguous monomers. Specific and preferred examples include phosphate groups (forming a phosphodiester between adjacent nucleoside monomers) and phosphorothioate groups (forming a phosphorothioate linkage between adjacent nucleoside monomers).

Suitable linkage groups include those listed in WO2007/031091, for example in the first paragraph of page 34 of WO2007/031091 (hereby incorporated by reference).

It is, in various embodiments, preferred to modify the linkage group from its normal phosphodiester to one that is more resistant to nuclease attack, such as phosphorothioate or boranophosphate—these two being cleavable by RNase H, thereby permitting RNase-mediated antisense inhibition of expression of the target gene.

In some embodiments, suitable sulphur (S) containing linkage groups as provided herein are preferred. In various embodiments, phosphorothioate linkage groups are preferred, particularly for the gap region (B) of gapmers. In certain embodiments, phosphorothioate linkages are used to link together monomers in the flanking regions (A and C). In various embodiments, phosphorothioate linkages are used for linking regions A or C to region D, and for linking together monomers within region D.

In various embodiments, regions A, B and C, comprise linkage groups other than phosphorothioate, such as phosphodiester linkages, particularly for instance when the use of nucleoside analogues protects the linkage groups within regions A and C from endo-nuclease degradation—such as when regions A and C comprise LNA monomers.

In various embodiments, adjacent monomers of the oligomer are linked to each other by means of phosphorothioate groups.

It is recognised that the inclusion of phosphodiester linkages, such as one or two linkages, into an oligomer with a phosphorothioate backbone, particularly with phosphorothioate linkage groups between or adjacent to nucleoside analogue monomers (typically in region A and/or C), can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such as those provided herein, it will be understood that, in various embodiments, when the linkages are phosphorothioate linkages, alternative linkages, such as those disclosed herein may be used, for example phosphate (phosphodiester) linkages may be used, particularly for linkages between nucleoside analogues, such as LNA monomers. Likewise, in various embodiments, when referring to specific gapmer oligonucleotide sequences, such as those provided herein, when one or more monomers in region A or C, such as LNA monomers, comprises a 5-methylcytosine base, other monomers in that region may contain unmodified cytosine bases.

Target Nucleic Acid

The terms "nucleic acid" and "polynucleotide" are used interchangeably herein, and are defined as a molecule formed by covalent linkage of two or more monomers, as above-described. Including 2 or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

The term "target nucleic acid", as used herein, refers to DNA or RNA (e.g., mRNA or pre-mRNA) encoding a mammalian Hsp27 polypeptide, such as human Hsp27, as the nucleic acid having the sequence shown in SEQ ID NO: 137, and naturally occurring allelic variants of such nucleic acids. In certain embodiments, the mammalian Hsp27 is a mouse Hsp27. In some embodiments, for example when used in research or diagnostics, the "target nucleic acid" is a cDNA or a synthetic oligonucleotide derived from the above DNA or RNA nucleic acid targets. The oligomers according to the invention are typically capable of hybridising to the target nucleic acid.

Exemplary target nucleic acids include mammalian Hsp27-encoding nucleic acids having the GenBank Accession numbers shown in the table below, along with their corresponding protein sequences:

|  | GenBank Accession Number Nucleic acid (mRNA/cDNA sequence) | GenBank Accession Number Polypeptide (deduced) |
| --- | --- | --- |
| Human | NM_001540 (SEQ ID No 137) | NP_001531 |
| Mouse | NM_024441 | NP_077761 |

It is recognised that the above-disclosed GenBank Accession numbers for nucleic acids refer to cDNA sequences and not to mRNA sequences per se. The sequence of a mature mRNA can be derived directly from the corresponding cDNA sequence with thymine bases (T) being replaced by uracil bases (U).

The term "naturally occurring variant thereof" refers to variants of the Hsp27 polypeptide or nucleic acid sequence which exist naturally within the defined taxonomic group, such as mammals, such as mouse, monkey, and preferably human Hsp27. Typically, when referring to "naturally occurring variants" of a polynucleotide the term also encompasses any allelic variant of the Hsp27 encoding genomic DNA which is found at Chromosome 7: 75.77-75.77 Mb by chromosomal translocation or duplication, and the RNA, such as mRNA derived therefrom. "Naturally occurring variants" may also include variants derived from alternative splicing of the Hsp27 mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

In certain embodiments, oligomers described herein bind to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Such binding is also referred to as "hybridisation." Unless otherwise indicated, binding is by Watson-Crick pairing of complementary bases (i.e., adenine with thymine (DNA) or uracil (RNA), and guanine with cytosine), and the oligomer binds to the target region because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" (homology) to the reverse complement of the sequence of the target region.

The terms "reverse complement", "reverse complementary" and "reverse complementarity" as used herein are interchangeable with the terms "complement", "complementary" and "complementarity".

Unless otherwise made clear by context, the "target region" herein will be the region of the target nucleic acid having the sequence that best aligns with the reverse complement of the sequence of the specified oligomer (or region thereof), using the alignment program and parameters described herein below.

In determining the degree of "complementarity" between oligomers of the invention (or regions thereof) and the target region of the nucleic acid which encodes mammalian Hsp27, such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

As used herein, the terms "homologous" and "homology" are interchangeable with the terms "identity" and "identical".

Amino acid and polynucleotide alignments, percentage sequence identity, and degree of complementarity may be determined for purposes of the invention using the ClustalW algorithm using standard settings: see http://www.ebi.ac.uk/emboss/align/index.html, Method: EMBOSS::water (local): Gap Open=10.0, Gap extend=0.5, using Blosum 62 (protein), or DNAfull for nucleotide/nucleobase sequences.

As will be understood, depending on context, "mismatch" refers to a non-identity in sequence (as, for example, between the nucleobase sequence of an oligomer and the reverse complement of the target region to which it binds; as for example, between the base sequence of two aligned Hsp27 encoding nucleic acids), or to noncomplementarity in sequence (as, for example, between an oligomer and the target region to which it binds).

In some embodiments, the oligomers according to the invention are capable of inhibiting (such as, by down-regulating) the expression of one or more Hsp27 target genes in a cell which is expressing, or is capable of expressing (i.e. by alleviating Hsp27 repression of the Hsp27 target gene in a cell) an Hsp27 target gene.

The oligomers which target Hsp27 mRNA, may hybridize to any site along the target mRNA nucleic acid, such as the 5' untranslated leader, exons, introns and 3' untranslated tail. However, it is preferred that the oligomers which target Hsp27 mRNA hybridise to the mature mRNA form of the target nucleic acid.

Suitably, the oligomer of the invention or conjugate thereof is capable of down-regulating (e.g. reducing or removing) expression of the Hsp27 gene. In various embodiments, the oligomer (or conjugate) of the invention can effect the inhibition of Hsp27, typically in a mammalian cell, such as a human cell. In certain embodiments, the oligomers of the invention, or conjugates thereof, bind to the target nucleic acid and affect inhibition of Hsp27 mRNA expression of at least 10% or 20% compared to the expression level in the absence of the oligomer(s) or conjugate(s), more preferably of at least 30%, 40%, 50%, 60%, 70%, 80%, 90% or 95% as compared to the Hsp27 expression level in the absence of the oligomer(s) or conjugate(s). In some embodiments, such inhibition is seen when using from about 0.04 nM to about 25 nM, such as from about 0.8 nM to about 20 nM of the oligomer or conjugate. As illustrated herein the cell type is, in some embodiments, a human cell, such as a cancer cell, such as a human lung cancer cell or a human prostate cancer cell (e.g. in vitro—transfected cells). The oligomer concentration used is, in some embodiments, 5 nM. The oligomer concentration used is, in some embodiments 25 nM. The oligomer concentration used is, in some embodiments 1 nM. It should be noted that the concentration of oligomer used to treat the cell is in various typical embodiments performed in an in vitro cell assay, using transfection (Lipofecton), as illustrated in the Examples. In the absence of a transfection agent, the oligomer concentration required to obtain the down-regulation of the target is typically between 1 and 25 µM, such as 5 µM.

In various embodiments, the inhibition of mRNA expression is less than 100% (i.e., less than complete inhibition of expression), such as less than 98% inhibition, less than 95% inhibition, less than 90% inhibition, less than 80% inhibition, such as less than 70% inhibition. In various embodiments, modulation of gene expression can be determined by measuring protein levels, e.g. by methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from about 0.04 nM to about 25 nM, such as from about 0.8 nM to about 20 nM, is, in various embodiments, typically to a level of 10-20% of the normal levels in the absence of the oligomer, conjugate or composition of the invention.

The invention therefore provides a method of down-regulating or inhibiting the expression of Hsp27 protein and/or mRNA in a cell which is expressing Hsp27 protein and/or mRNA, the method comprising contacting the cell with an effective amount of the oligomer or conjugate according to the invention to down-regulate or inhibit the expression of the Hsp27 protein and/or mRNA in the cell. Suitably the cell is a mammalian cell, such as a human cell. The contacting may occur, in some embodiments, in vitro. The contacting may occur, in some embodiments, in vivo.

Oligomer Sequences

In some embodiments, the oligomers of the invention have sequences that are identical to a sequence selected from the group consisting of SEQ ID NOs: 1 to 128.

Further provided are target nucleic acids (e.g., DNA or mRNA encoding Hsp27) that contain target regions that are (fully or perfectly) complementary or partially-complementary to one or more of the oligomers of the invention. In certain embodiments, the oligomers bind to variants of Hsp27 target regions, such as allelic variants (such as an Hsp27 gene present at gene locus Chromosome 7: 75.77-75.77 Mb). In some embodiments, a variant of an Hsp27 target region has at least 60%, more preferably at least 70%, more preferably at least 80%, more preferably at least 85%, more preferably at least 90%, more preferably at least 91%, at least 92%, at least 93%, at least 94%, at least 95%, at least 96%, at least 97%, at least 98%, at least 99% sequence identity to the target region having a sequence set forth in SEQ ID NO: 137. Thus, in other embodiments, the oligomers of the invention have sequences that differ in 1, 2 or 3 bases when compared to a sequence selected from the group consisting of SEQ ID NOs: 1 to 128. Typically, an oligomer of the invention that binds to a variant of an Hsp27 target region is capable of inhibiting (e.g., by down-regulating) Hsp27.

In other embodiments, oligomers of the invention are LNA oligomers, for example, those oligomers having the sequences shown in SEQ ID NOs: 129-136. In various embodiments, the oligomers of the invention are potent inhibitors of Hsp27 mRNA and protein expression. In some embodiments, the phrase "potent inhibitor" refers to an oligomer with an I050 of less than 5 nM as determined by the lipofectamine transfection assay of Example 5. In some embodiments, the I050 is less than 4 nM, such as less than 2 nM.

In various embodiments, oligomers of the invention are LNA oligomers having the sequences of SEQ ID NO: 131 or SEQ ID NO: 135.

In various embodiments, the oligomer comprises or consists of a first region having a base sequence which is identical or partially identical to the sequence of the reverse complement of a target region in SEQ ID NO: 137. In various embodiments, the oligomer comprises or consists of a first region having a sequence selected from the group consisting of SEQ ID NOS: 1-128.

In certain embodiments, the oligomer comprises or consists of a first region having a base sequence which is fully complementary (perfectly complementary) to the sequence of a target region of a nucleic acid which encodes a mammalian Hsp27.

However, in some embodiments, the oligomer includes 1, 2, 3, or 4 (or more) mismatches as compared to the best-aligned target region of an Hsp27 target nucleic acid, and still sufficiently binds to the target region to effect inhibition of Hsp27 mRNA or protein expression. The destabilizing effect of mismatches on Watson-Crick hydrogen-bonded duplex may, for example, be compensated by increased length of the oligomer and/or an increased number of nucleoside analogues, such as LNA monomers, present within the oligomer.

In various embodiments, the oligomer base sequence comprises no more than 3, such as no more than 2 mismatches compared to the base sequence of the best-aligned target region of, for example, a target nucleic acid which encodes a mammalian Hsp27.

In some embodiments, the oligomer base sequence comprises no more than a single mismatch when compared to the base sequence of the best-aligned target region of a nucleic acid which encodes a mammalian Hsp27.

In various embodiments, the base sequence of the oligomer of the invention, or of a first region thereof, is preferably at least 80% identical to a base sequence selected from the group consisting of SEQ ID NOS: 1-15 and 121, 16-30 and 122, 31-45 and 123, 46-60 and 124, 61-75 and 125, 76-90 and 126, 91-105, and 127, and 106-120 and 128, such as at least 85%, at least 90%, at least 91%, at least 92%, at least 93%, at least 94%, at least 95%, at least 96%, at least 97%, at least 98%, at least 99% identical, such as 100% identical.

In certain embodiments, the base sequence of the oligomer of the invention or of a first region thereof is at least 80% identical to the base sequence of the reverse complement of a target region present in SEQ ID NO: 137, such as at least 85%, at least 90%, at least 91%, at least 92%, at least 93%, at least 94%, at least 95%, at least 96% identical, at least 97% identical, at least 98% identical, at least 99% identical, such as 100% identical.

In various embodiments, the base sequence of the oligomer of the invention, or of a first region thereof, is preferably at least 80% complementary to a target region of SEQ ID NO: 137, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments the oligomer (or a first region thereof) has a base sequence selected from the group consisting of SEQ ID NOs: 1, 16, 31, 46, 61, 76, 91, and 106, or is selected from the group consisting of at least 9 or 10 contiguous monomers of SEQ ID NOs: 1, 16, 31, 46, 61, 76, 91, and 106. In other embodiments, the sequence of the oligomer of the invention or a first region thereof comprises one, two, or three base moieties that differ (e.g. are mismatches) from those in oligomers having sequences of SEQ ID NOs: 1, 16, 31, 46, 61, 76, 91, and 106, or the sequences of at least 9 or 10 contiguous monomers thereof, when optimally aligned with the selected sequence or region thereof.

In some embodiments, the term "first region" as used herein refers to a portion (sub-sequence) of an oligomer. For example, the 16 monomer sequence set forth in SEQ ID NO: 1 is a subsequence of the 24 monomer sequence set forth in SEQ ID NO: 121, i.e., the sequence set forth in SEQ ID NO: 121 comprises the sequence set forth in SEQ ID NO: 1.

In some embodiments the oligomer (or a first region thereof) has a base sequence selected from the group consisting of SEQ ID NOs: 121-128, or the sequences of at least 9 or 10 contiguous monomers thereof. In other embodiments, the sequence of the oligomer (or a first region thereof) comprises one, two, or three base moieties that differ from those in oligomers having sequences of SEQ ID NOs: 121-128, or the sequences of at least 9 or 10 contiguous monomers thereof, when optimally aligned with the selected sequence or region thereof.

In various embodiments, the oligomers comprise a region of 9, 10, 11, 12, 13, 14, 15 or 16 contiguous monomers, such as 12-16, having a base sequence identically present in a sequence selected from the group consisting of SEQ ID No 1, 16, 31, 46, 61, 76, 91, and 106. In other embodiments, the oligomers include a region which comprises one, two, or three base moieties that differ from those in oligomers having sequences of SEQ ID NOs: 1, 16, 31, 46, 61, 76, 91, and 106.

In some embodiments the first region consists of 9, 10, 11, 12, 13, 14, 15, 16, 17, 18, 19, 20, 21, 22, 23, 24, 25, 26, 27, 28, or 29 contiguous monomers, such as 9-22, such as 12-24, such as 12-22, such as 12-18, such as 12-16 monomers. Suitably, in some embodiments, the first region is of the same length as the oligomer of the invention.

In some embodiments the oligomer comprises additional monomers at the 5' and/or 3' ends of the first region, such as, independently, 1, 2, 3, 4 or 5 additional monomers at the 5' end and/or the 3' end of the oligomer, which are non-complementary to the target region. In various embodiments, the oligomer of the invention comprises a first region that is complementary to the target, which is flanked 5' and/or 3' by additional monomers which are complementary to the target region. In some embodiments the additional 5' or 3' monomers are nucleosides, such as DNA or RNA monomers. In various embodiments, the 5' or 3' monomers represent region D as referred to in the context of gapmer oligomers herein.

In some embodiments the oligomer according to the invention consists of or comprises contiguous monomers (a first region) having a nucleobase sequence according to SEQ ID NO:121, or at least 9 contiguous monomers thereof such as 10, 11, 12, 13, 14, 15 or 16 contiguous monomers thereof, such as SEQ ID NOs 1-15.

In some embodiments the oligomer according to the invention consists of or comprises contiguous monomers (a first region) having a nucleobase sequence according to SEQ ID NO:122, or at least 9 contiguous monomers thereof such as 10, 11, 12, 13, 14, 15 or 16 contiguous monomers thereof, such as SEQ ID NOs 16-30.

In some embodiments the oligomer according to the invention consists of or comprises contiguous monomers (a first region) having a nucleobase sequence according to SEQ ID NO:123, or at least 9 contiguous monomers thereof such as 10, 11, 12, 13, 14, 15 or 16 contiguous monomers thereof, such as SEQ ID NOs 31-45.

In some embodiments the oligomer according to the invention consists of or comprises contiguous monomers (a first region) having a nucleobase sequence according to SEQ ID NO:124, or at least 9 contiguous monomers thereof such as 10, 11, 12, 13, 14, 15 or 16 contiguous monomers thereof, such as SEQ ID NOs 46-60.

In some embodiments the oligomer according to the invention consists of or comprises contiguous monomers (a first region) having a nucleobase sequence according to SEQ ID NO:125, or at least 9 contiguous monomers thereof such as 10, 11, 12, 13, 14, 15 or 16 contiguous monomers thereof, such as SEQ ID NOs 61-75.

In some embodiments the oligomer according to the invention consists of or comprises contiguous monomers (a first region) having a nucleobase sequence according to SEQ ID NO:126, or at least 9 contiguous monomers thereof such as 10, 11, 12, 13, 14, 15 or 16 contiguous monomers thereof, such as SEQ ID NOs 76-90.

In some embodiments the oligomer according to the invention consists of or comprises contiguous monomers (a first region) having a nucleobase sequence according to SEQ ID NO:127, or at least 9 contiguous monomers thereof such as 10, 11, 12, 13, 14, 15 or 16 contiguous monomers thereof, such as SEQ ID NOs 91-105.

In some embodiments the oligomer according to the invention consists of or comprises contiguous monomers (a first region) having a nucleobase sequence according to SEQ ID NO:128, or at least 9 contiguous monomers thereof such as 10, 11, 12, 13, 14, 15 or 16 contiguous monomers thereof, such as SEQ ID NO 106-120.

Nucleosides and Nucleoside Analogues

In some embodiments, the terms "nucleoside analogue" and "nucleotide analogue" are used interchangeably.

In various embodiments, at least one of the monomers present in the oligomer is a nucleoside analogue that contains a modified base, such as a base selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In various embodiments, at least one of the monomers present in the oligomer is a nucleoside analogue that comprises a modified sugar.

In some embodiments, the linkage between at least 2 contiguous monomers of the oligomer is other than a phosphodiester linkage.

In certain embodiments, the oligomer includes at least one monomer that has a modified base, at least one monomer (which may be the same monomer) that has a modified sugar, and at least one inter-monomer linkage that is non-naturally occurring.

Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1 (in which some nucleoside analogues are shown as nucleotides)

Scheme 1

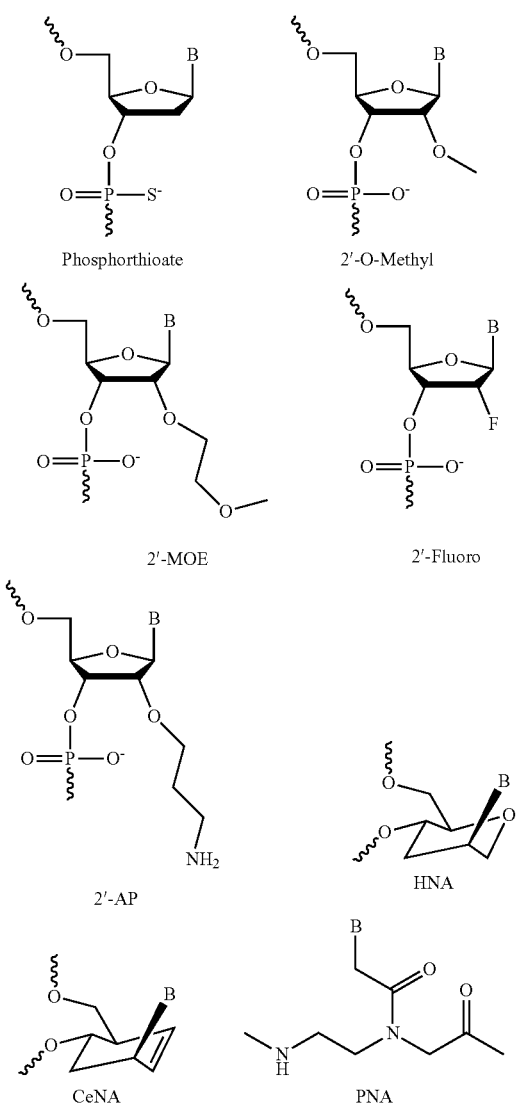

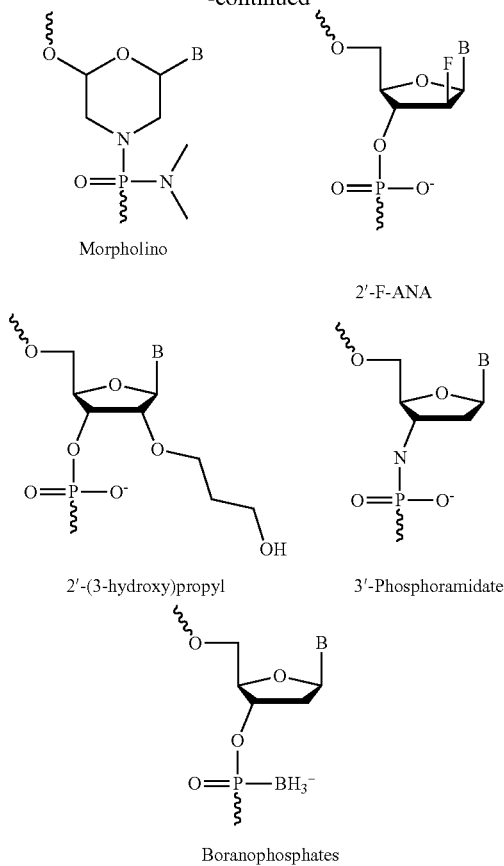

Morpholino

2'-F-ANA

2'-(3-hydroxy)propyl

3'-Phosphoramidate

Boranophosphates

The oligomer may thus comprise or consist of a simple sequence of naturally occurring nucleosides—preferably DNA monomers, but also possibly RNA monomers, or a combination of nucleosides and one or more nucleoside analogues. In some embodiments, such nucleoside analogues suitably enhance the affinity of the oligomer for the target region of the target nucleic acid.

Examples of suitable and preferred nucleoside analogues are described in WO2007/031091, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a bicyclic sugar (LNA), which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In certain embodiments, the LNA monomers are beta-D-oxy-LNA. LNA monomers are further described below.

In various embodiments, incorporation of affinity-enhancing nucleoside analogues in the oligomer, such as LNA monomers or monomers containing 2'-substituted sugars, or incorporation of modified linkage groups provides increased nuclease resistance. In various embodiments, incorporation of affinity-enhancing nucleoside analogues allows the size of the oligomer to be reduced, and also reduces the size of the oligomer that binds specifically to a target region of a target sequence.

In some embodiments, the oligomer comprises at least 1 nucleoside analogue. In some embodiments, the oligomer comprises at least 2 nucleoside analogues. In some embodiments, the oligomer comprises from 3-8 nucleoside analogues, e.g. 6 or 7 nucleoside analogues. In various embodiments, at least one of the nucleoside analogues is a locked nucleic acid (LNA) monomer; for example at least 3 or at least 4, or at least 5, or at least 6, or at least 7, or 8, nucleoside analogues are LNA monomers. In some embodiments, all the nucleoside analogues are LNA monomers.

It will be recognised that when referring to a preferred oligomer base sequence, in certain embodiments, the oligomers comprise a corresponding nucleoside analogue, such as a corresponding LNA monomer or other corresponding nucleoside analogue, which raises the duplex stability ($T_m$) of the oligomer/target region duplex (i.e. affinity enhancing nucleoside analogues).

In various embodiments, any mismatches (i.e., non-complementarities) between the base sequence of the oligomer and the base sequence of the target region, if present, are preferably located other than in the regions of the oligomer that contain affinity-enhancing nucleoside analogues (e.g., regions A or C), such as within region B as referred to herein, and/or within region D as referred to herein, and/or in regions consisting of DNA monomers, and/or in regions which are 5' or 3' to the region of the oligomer that is complementary to the target region.

In some embodiments the nucleoside analogues present within the oligomer of the invention (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-arabinose sugars, monomers containing d-arabino-hexitol sugars ("HNA monomers"), intercalating monomers as defined in Christensen (2002) Nucl. Acids. Res. 30: 4918-4925, hereby incorporated by reference, and 2'-O-methoxyethyl-ribose (2'MOE) sugars. In some embodiments, there is only one of the above types of nucleoside analogues present in the oligomer of the invention, or region thereof.

In certain embodiments, the nucleoside analogues contain 2'MOE sugars, 2'-fluoro-deoxyribose sugars, or LNA sugars, and as such the oligomer of the invention may comprise nucleoside analogues which are independently selected from these three types. In certain oligomer embodiments containing nucleoside analogues, at least one of said nucleoside analogues contains a 2'-MOE-ribose sugar, such as 2, 3, 4, 5, 6, 7, 8, 9 or 10 nucleoside analogues containing 2'-MOE-ribose sugars. In some embodiments, at least one nucleoside analogue contains a 2'-fluoro-deoxyribose sugar, such as 2, 3, 4, 5, 6, 7, 8, 9 or 10 nucleoside analogues containing 2'-fluoro-DNA nucleotide sugars.

In various embodiments, the oligomer according to the invention comprises at least one Locked Nucleic Acid (LNA) monomer, such as 1, 2, 3, 4, 5, 6, 7, or 8 LNA monomers, such as 3-7 or 4 to 8 LNA monomers, or 3, 4, 5, 6 or 7 LNA monomers. In various embodiments, all the nucleoside analogues are LNA monomers. In certain embodiments, the oligomer comprises both beta-D-oxy-LNA monomers, and one or more of the following LNA monomers: thio-LNA monomers, amino-LNA monomers, oxy-LNA monomers, and/or ENA monomers in either the beta-D or alpha-L configurations, or combinations thereof. In certain embodiments, the cytosine base moieties of all LNA monomers in the oligomer are 5-methylcytosines. In certain embodiments of the invention, the oligomer comprises both LNA and DNA monomers. Typically, the combined total of LNA and DNA monomers is 10-25, preferably 10-24, preferably 10-20, preferably 10-18, even more preferably 12-16. In some embodiments of the invention, the oligomer or region thereof consists of at least one LNA monomer, and the remaining monomers are DNA monomers. In certain embodiments, the oligomer comprises only LNA monomers and nucleosides (such as RNA or DNA monomers, most preferably DNA monomers) optionally with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" or "LNA monomer" refers to a bicyclic nucleoside analogue, known as "Locked Nucleic Acid". When used in the context of an "LNA oligonucleotide", LNA refers to an oligonucleotide containing one or more such bicyclic nucleoside analogues. LNA nucleosides are characterised by the presence of a linker group (such as a bridge) between C2' and C4' of the ribose sugar ring to form a bicyclic system—for example between the $R^{4*}$ and $R^{2*}$ groups as described below.

The LNA used in the oligonucleotide compounds (oligomers) of the invention preferably has the structure of the general formula I

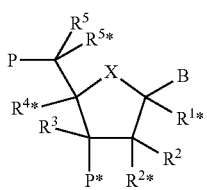

Formula 1 wherein for all chiral centers, asymmetric groups may be found in either R or S orientation;

wherein X is selected from —O—, —S—, —N($R^{N*}$)— and —O($R^6R^{6*}$)—, more preferably —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleoside linkage to an adjacent monomer, or a 5'-terminal group, said internucleoside linkage or 5'-terminal group optionally including the substituent $R^5$ or equally applicable the substituent $R^{5*}$;

P* designates an internucleoside linkage to an adjacent monomer, or a 3'-terminal group;

$R^{4*}$ and $R^{2*}$ together form a bivalent linker group, such as, for example, a biradical consisting of 1-4 groups/atoms each independently selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ are each independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where each aryl and heteroaryl may be optionally substituted and where two geminal substituents $R^a$ and $R^b$ together may form an optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$ is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where each aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and basic salts and acid addition salts thereof. For all chiral centers, asymmetric groups may be found in either R or S orientation.

Where the definitions used herein refer to substituted $C_{1-4}$-alkyl, substituted $C_{1-6}$ alkyl, substituted $C_{1-12}$-alkyl, substituted $C_{2-12}$-alkenyl, substituted $C_{2-6}$ alkenyl, substituted $C_{2-12}$-alkynyl, substituted $C_{2-6}$ alkynyl, substituted $C_{1-12}$-alkoxy, substituted $C_{1-6}$alkoxy, substituted $C_{1-4}$-alkoxy, substituted $C_{1-4}$-acyloxy, substituted aryl, substituted heteroaryl, substituted methylene, substituted acyl, substituted $C_{1-6}$ aminoalkyl or substituted amide, suitable substituents preferably include one or more $R^g$ groups, wherein each $R^g$ is independently selected from halogen, $C_{1-6}$ alkyl, substituted $C_{1-6}$alkyl, $C_{2-6}$ alkenyl, substituted $C_{2-6}$ alkenyl, $C_{2-6}$ alkynyl, substituted $C_{2-6}$ alkynyl, CN, OJ$_1$, SJ$_1$, NJ$_1$J$_2$, N$_3$, COOJ$_1$, C(=X)J$_1$, C(=X)NJ$_1$J$_2$, CN, O—C(=O)NJ$_1$J$_2$, O—C(=X) J$_1$, NJ$_1$C(=NH)NJ$_1$J$_2$ and NJ$_1$C(=X)NJ$_1$J$_2$ wherein X is O or S; and each J$_1$ and J$_2$ is independently selected from H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl and a protecting group. Preferably, each $R^g$ is independently selected from halogen, $C_{1-6}$ alkyl, $C_{2-6}$ alkenyl, $C_{2-6}$ alkynyl, CN, OJ$_1$, SJ$_1$, NJ$_1$J$_2$, N$_3$, COOJ$_1$, C(=X)J$_1$, C(=X)NJ$_1$J$_2$, CN, O—C(=O)NJ$_1$J$_2$, O—C(=X)J$_1$, NJ$_1$C(=NH)NJ$_1$J$_2$ and NJ$_1$C(=X)NJ$_1$J$_2$ wherein X is O or S; and each J$_1$ and J$_2$ is independently selected from H, $C_{1-6}$ alkyl, $C_{2-6}$ alkenyl, $C_{2-6}$ alkynyl, $C_{1-6}$ aminoalkyl and a protecting group. Suitable protecting groups are described in "Protective Groups in Organic Synthesis" by Theodora W Greene and Peter G M Wuts, 3rd edition (John Wiley & Sons, 1999).

In some embodiments, $R^{4*}$ and $R^{2*}$ together form a linker group selected from $C(R^aR^b)$—$C(R^aR^b)$—, $C(R^aR^b)$—O—, $C(R^aR^b)$—$NR^a$—, $C(R^aR^b)$—S—, and $C(R^aR^b)$—C($R^aR^b$)—O—, wherein $R^a$ and $R^b$ are as defined above. In some embodiments, $R^a$ and $R^b$ are each independently selected from hydrogen and $C_{1-6}$alkyl, and are more preferably each independently selected from hydrogen and methyl.

In some embodiments, $R^{1*}, R^2, R^3, R^5, R^{5*}$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl. For all chiral centers, asymmetric groups may be found in either R or S orientation.

In some preferred embodiments, $R^{1*}, R^2, R^3, R^5, R^{5*}$ are all hydrogen.

In some embodiments, $R^{1*}, R^2, R^3$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl. For all chiral centers, asymmetric groups may be found in either R or S orientation.

In some preferred embodiments, $R^{1*}, R^2, R^3$ are all hydrogen.

In some embodiments, $R^5$ and $R^{5*}$ are each independently selected from H, —$CH_3$, —$CH_2$—$CH_3$, —$CH_2$—O—$CH_3$, and —CH=$CH_2$. Preferably, in some embodiments, either $R^5$ or $R^{5*}$ is hydrogen, and the other group ($R^5$ or $R^{5*}$ respectively) is selected from $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl and substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(=O)$NJ_1J_2$, N(H)C(=NH)$NJ_1J_2$ and N(H)C(=X)N(H)$J_2$ wherein X is O or S; and each $J_1$ and $J_2$ is independently selected from H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl and a protecting group. In some embodiments either $R^5$ or $R^{5*}$ is substituted $C_{1-6}$ alkyl. In some embodiments either $R^5$ or $R^{5*}$ is substituted methylene, wherein preferred substituent groups include one or more groups independently selected from F, $NJ_1J_2$, $N_3$, CN, $OJ_1$, $SJ_1$, O—C(=O)$NJ_1J_2$, N(H)C(=NH)$NJ_1J_2$ and N(H)C(O)N(H)$J_2$. In some embodiments each $J_1$ and $J_2$ is independently H or $C_{1-6}$ alkyl. In some embodiments either $R^5$ or $R^{5*}$ is methyl, ethyl or methoxymethyl. In some embodiments either $R^5$ or $R^{5*}$ is methyl. In some embodiments either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Examples of such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, or a nucleobase selected from adenine, cytosine, thymine, adenine, uracil, and/or a modified or substituted nucleobase, such as 5-thiazolo-uracil, 2-thio-uracil, 5-propynyl-uracil, 2' thio-thymine, 5-methyl cytosine, 5-thiozolo-cytosine, 5-propynyl-cytosine and 2,6-diaminopurine.

In some embodiments, $R^{4*}$ and $R^{2*}$ together form a linker group selected from —$C(R^aR^b)$—O—, —$C(R^aR^b)$—C($R^bR^d$)—O—, —$C(R^aR^b)$—$C(R^bR^d)$—$C(R^eR^f)$—O—, —$C(R^aR^b)$—O—$C(R^bR^d)$—, —$C(R^aR^b)$—O—$C(R^bR^d)$—O—, —$C(R^aR^b)$—$C(R^bR^d)$—, —$C(R^aR^b)$—$C(R^bR^d)$—C($R^eR^f$)—, $C(R^a)$=$C(R^b)$—$C(R^bR^d)$—, —$C(R^aR^b)$—N($R^b$)—, —$C(R^aR^b)$—$C(R^bR^d)$—N($R^e$)—, —$C(R^aR^b)$—N($R^b$)—O—, —$C(R^aR^b)$—S— and —$C(R^aR^b)$—$C(R^bR^d)$—S—, wherein $R^a, R^b, R^c, R^d, R^e$, and $R^f$ are each independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where each aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In some embodiments $R^{4*}$ and $R^{2*}$ together designate a linker group selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, —CH($CH_2$—O—$CH_3$)—O—, —$CH_2$—$CH_2$— and —CH=CH—. For all chiral centers, asymmetric groups may be found in either R or S orientation.

In some embodiments, $R^{4*}$ and $R^{2*}$ together form a linker group $C(R^aR^b)$—N($R^c$)—O—, wherein $R^a$ and $R^b$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl, more preferably $R^a$ and $R^b$ are hydrogen, and; wherein $R^c$ is selected from hydrogen, halogen, $C_{1-6}$alkyl, substituted $C_{1-6}$alkyl, $C_{2-6}$ alkenyl, substituted $C_{2-6}$alkenyl, $C_{2-6}$ alkynyl, substituted $C_{2-6}$ alkynyl, $C_{1-6}$ alkoxy, substituted $C_{1-6}$alkoxy, acyl, substituted acyl, $C_{1-6}$ aminoalkyl, substituted $C_{1-6}$ aminoalkyl, and more preferably $R^c$ is hydrogen.

In some embodiments, $R^{4*}$ and $R^{2*}$ together form a linker group $C(R^aR^b)$—O—$C(R^cR^d)$—O—, wherein $R^a, R^b, R^c$, and $R^d$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$alkoxy, substituted $C_{1-6}$alkoxy, acyl, substituted acyl, $C_{1-6}$ aminoalkyl, substituted $C_{1-6}$ aminoalkyl, and more preferably $R^a, R^b, R^c$, and $R^d$ are hydrogen.

In some embodiments, $R^{4*}$ and $R^{2*}$ form a linker group —CH(Z)—O—, wherein Z is selected from $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol and substituted thiol; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ^3C(=X)NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Examples of such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are all hydrogen. In some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together form a linker group which comprises a substituted amino group, for example, $R^{4*}$ and $R^{2*}$ together form a linker group that consists of, or comprises, the group —$CH_2$—$N(R^c)$—, wherein $R^b$ is $C_{1-12}$ alkyloxy. In some embodiments $R^{4*}$ and $R^{2*}$ together form a linker group —$Cq_3q_4$-NOR—, wherein $q_3$ and $q_4$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—$C(=O)NJ_1J_2$, $N(H)C(=NH)NJ_1J_2$ and $N(H)C(=X)=N(H)J_2$ wherein X is O or S; and each of $J_1$ and $J_2$ is independently selected from H, $C_{1-6}$ alkyl, $C_{2-6}$ alkenyl, $C_{2-6}$ alkynyl, $C_{1-6}$ aminoalkyl and a protecting group. For all chiral centers, asymmetric groups may be found in either R or S orientation. Examples of such bicyclic nucleotides are disclosed in WO2008/150729 which is hereby incorporated by reference in its entirety. In some embodiments, $R^{1*}$, $R^2$, $R^3$, $R^5$, $R^{5*}$ are each independently selected from hydrogen, halogen, $C_{1-6}$ alkyl, substituted $C_{1-6}$ alkyl, $C_{2-6}$alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl. In some embodiments, $R^{1*}$, $R^2$, $R^3$, $R^5$, $R^{5*}$ are all hydrogen. In some embodiments, $R^{1*}$, $R^2$, $R^3$ are all hydrogen and one or both of $R^5$, $R^{5*}$ may be other than hydrogen as referred to above and in WO 2007/134181. In some embodiments $R^{4*}$ and $R^{2*}$ together form a linker group $C(R^aR^b)$—O—, wherein $R^a$ and $R^b$ are each independently selected from halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1SJ_1$, $SOJ_1$, $SO_2J_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=NH)NJ_1J_2$, $N(H)C(=O)NJ_1J_2$ and $N(H)C(=S)NJ_1J_2$; or $R^a$ and $R^b$ together are $=C(q_3)(q_4)$; $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)NJ_1J_2$ and $N(H)C(=S)NJ_1J_2$; each $J_1$ and $J_2$ is independently selected from H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl and a protecting group. Such compounds are disclosed in WO2009/006478, hereby incorporated in its entirety by reference.

In some embodiments, $R^{4*}$ and $R^{2*}$ form a linker group-Q-, wherein Q is $C(q_1)(q_2)C(q_3)(q_4)$, $C(q_1)=C(q_3)$, $C[=C(q_1)(q_2)]$—$C(q_3)(q_4)$ or $C(q_1)(q_2)$—$C[=C(q_3)(q_4)]$; $q_1$, $q_2$, $q_3$, $q_4$ are each independently selected from H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, $C(=O)OJ_1$, $C(=O)$—$NJ_1J_2$, $C(=O)$ $J_1$, —$C(=O)NJ_1J_2$, $N(H)C(=NH)NJ_1J_2$, $N(H)C(=O)NJ_1J_2$ and $N(H)C(=S)NJ_1J_2$; each $J_1$ and $J_2$ is independently selected from H, $C_{1-6}$ alkyl, $C_{2-6}$ alkenyl, $C_{2-6}$ alkynyl, $C_{1-6}$ aminoalkyl and a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are all hydrogen. For all chiral centers, asymmetric groups may be found in either R or S orientation. Examples of such bicyclic nucleotides are disclosed in WO2008/154401 which is hereby incorporated by reference in its entirety. In some embodiments, $R^{1*}$, $R^2$, $R^3$, $R^5$, $R^{5*}$ are each independently selected from hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ alkoxy, substituted $C_{1-6}$ alkoxy, acyl, substituted acyl, $C_{1-6}$ aminoalkyl and substituted $C_{1-6}$ aminoalkyl. In some embodiments, $R^{1*}$, $R^2$, $R^3$, $R^5$, $R^{5*}$ are all hydrogen. In some embodiments, $R^{1*}$, $R^2$, $R^3$ are all hydrogen and one or both of $R^5$, $R^{5*}$ may be other than hydrogen as referred to above and in WO 2007/134181 or WO2009/067647 (alpha-L-bicyclic nucleic acids analogs).

In some preferred embodiments the LNA monomer present in the oligonucleotide compounds of the invention preferably has the structure of the general formula II:

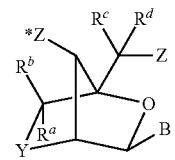

Formula II wherein Y is selected from —O—, —$CH_2O$—, —S—, —NH—, $N(R^e)$ and —$CH_2$—; Z and Z* are each independently selected from an internucleoside linkage, $R^H$, a terminal group and a protecting group; B constitutes a natural or non-natural nucleotide base moiety (nucleobase), and $R^H$ is selected from hydrogen and $C_{1-4}$-alkyl; $R^a$, $R^bR^c$, $R^d$ and $R^e$ are each independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where each aryl and heteroaryl may be optionally substituted and where two geminal substituents $R^a$ and $R^b$ together may designate optionally substituted methylene (=CH$_2$); and R$^H$ is selected from hydrogen and C$_{1-4}$-alkyl. In some preferred embodiments R$^a$, R$^b$R$^c$, R$^d$ and R$^e$ are each independently selected from hydrogen and C$_{1-6}$ alkyl, more preferably methyl. For all chiral centers, asymmetric groups may be found in either R or S orientation, for example, two exemplary stereochemical isomers include the beta-D and alpha-L isoforms, which may be illustrated as follows:

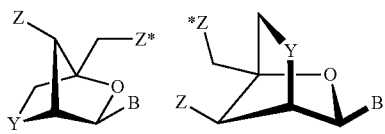

Specific exemplary LNA units are shown below (in Scheme 2):

Scheme 2

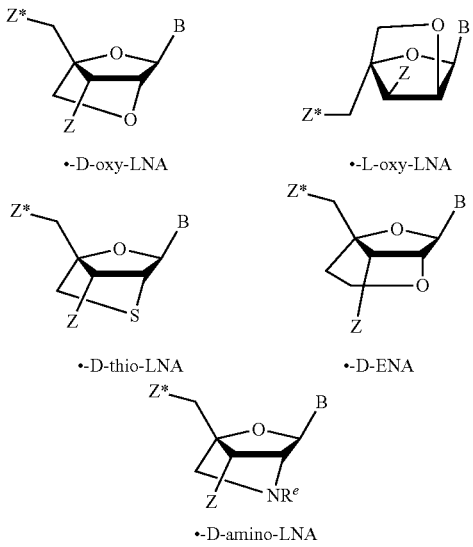

•-D-oxy-LNA      •-L-oxy-LNA

•-D-thio-LNA      •-D-ENA

•-D-amino-LNA

The term "thio-LNA" comprises a locked nucleoside in which Y in the general formula above is selected from S or —CH$_2$—S—. Thio-LNA can be in both beta-D and alpha-L-configuration.

The term "amino-LNA" comprises a locked nucleoside in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleoside in which Y in the general formula above represents —O—. Oxy-LNA can be in both beta-D and alpha-L-configuration.

The term "ENA" comprises a locked nucleoside in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

RNAse H Recruitment

In some embodiments, an oligomer functions via non-RNase-mediated degradation of a target mRNA, such as by steric hindrance of translation, or other mechanisms; however, in various embodiments, oligomers of the invention are capable of recruiting one or more RNAse enzymes or complexes, such as endo-ribonuclease (RNase), such as RNase H.

Typically, the oligomer, comprises a region of at least 6, such as at least 7 contiguous monomers, such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein. In some embodiments, the region of the oligomer which is capable of recruiting RNAse, such as region B, consists of 9, 10, 11, 12, 13, 14, 15, 16, 17, 18, 19 or 20 monomers.

EP 1 222 309 provides in vitro methods for determining RNaseH activity, which may be used to determine the ability of the oligomers of the invention to recruit RNaseH. An oligomer is deemed capable of recruiting RNaseH if, when contacted with the complementary region of the RNA target, it has an initial rate, as measured in pmol/l/min, of at least 1%, such as at least 5%, such as at least 10% or more than 20% of the initial rate determined using an oligonucleotide having the same base sequence but containing only DNA monomers, with no 2' substitutions, with phosphorothioate linkage groups between all monomers in the oligonucleotide, using the methodology provided by Examples 91-95 of EP 1 222 309, incorporated herein by reference.

In some embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

Typically, the region of the oligomer which forms the duplex with the complementary target region of the target RNA and is capable of recruiting RNase contains DNA monomers and optionally LNA monomers and forms a DNA/RNA-like duplex with the target region. The LNA monomers are preferably in the alpha-L configuration, particularly preferred being alpha-L-oxy LNA.

In various embodiments, the oligomer of the invention comprises both nucleosides and nucleoside analogues, and is in the form of a gapmer, a headmer or a mixmer.

A "headmer" is defined as an oligomer that comprises a region X and a region Y that is contiguous thereto, with the 5'-most monomer of region Y linked to the 3'-most monomer of region X. Region X comprises a contiguous stretch of non-RNase recruiting nucleoside analogues and region Y comprises a contiguous stretch (such as at least 7 contiguous monomers) of DNA monomers or nucleoside analogue monomers recognizable and cleavable by the RNase.

A "tailmer" is defined as an oligomer that comprises a region X and a region Y that is contiguous thereto, with the 5'-most monomer of region Y linked to the 3'-most monomer of the region X. Region X comprises a contiguous stretch (such as at least 7 contiguous monomers) of DNA monomers or nucleoside analogue monomers recognizable and cleavable by the RNase, and region Y comprises a contiguous stretch of non-RNase recruiting nucleoside analogues.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNaseH) binding and cleavage. Since .-L-LNA monomers recruit RNaseH activity to a certain extent, in some embodiments, gap regions (e.g., region B as referred to herein) of oligomers containing .-L-LNA monomers consist of fewer monomers recognizable and cleavable by the RNaseH, and more flexibility in the mixmer construction is introduced.

Conjugates e.g., dodecandiol or undecyl residues, a phospholipid, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

In certain embodiments, the oligomers of the invention are conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptide of, for example 1-50, such as 2-20 such as 3-10 amino acid residues in length, and/or polyalkylene oxide such as polyethylene glycol (PEG) or polypropylene glycol—see WO 2008/034123, hereby incorporated by reference. Suitably the positively charged polymer, such as a polyalkylene oxide may be attached to the oligomer of the invention via a linker such as the releasable linker described in WO 2008/034123.

By way of example, the following moieties may be used in the conjugates of the invention:

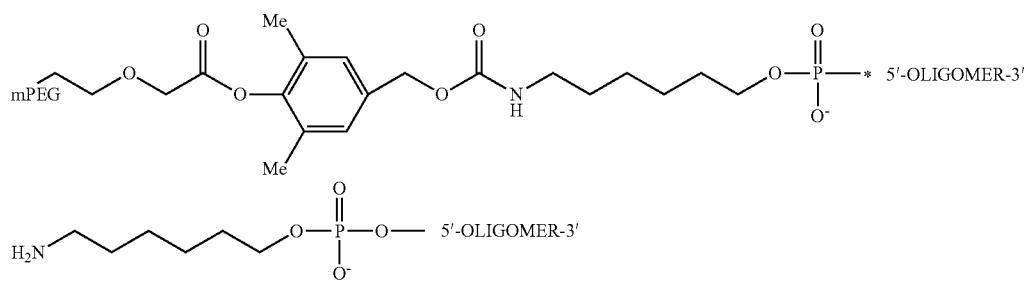

In the context of this disclosure, the term "conjugate" indicates a compound formed by the covalent attachment ("conjugation") of an oligomer as described herein, to one or more moieties that are not themselves nucleic acids or monomers ("conjugated moieties"). Examples of such conjugated moieties include macromolecular compounds such as proteins, fatty acid chains, sugar residues, glycoproteins, polymers, or combinations thereof. Typically proteins may be antibodies for a target protein. Typical polymers may be polyethylene glycol.

Accordingly, provided herein are conjugates comprising an oligomer as herein described, and at least one conjugated moiety that is not a nucleic acid or monomer, covalently attached to said oligomer. Therefore, in certain embodiments where the oligomer of the invention consists of contiguous monomers having a specified sequence of bases, as herein disclosed, the conjugate may also comprise at least one conjugated moiety that is covalently attached to the oligomer.

In various embodiments of the invention, the oligomer is conjugated to a moiety that increases the cellular uptake of oligomeric compounds. WO2007/031091 provides suitable ligands and conjugates (moieties), which are hereby incorporated by reference.

In various embodiments, conjugation (to a conjugated moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, Activated Oligomers The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W. Greene and Peter G. M. Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are activated (i.e. functionalized) at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis.

In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH). In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular, by methods disclosed in PCT Publication No. WO 2008/034122 and the examples therein, which is incorporated herein by reference in its entirety.

Activated oligomers covalently linked to at least one functional moiety can be synthesized by any method known in the art, and in particular, by methods disclosed in U.S. Patent Publication No. 2004/0235773, which is incorporated herein by reference in its entirety, and in Zhao et al. (2007) J. Controlled Release 119:143-152; and Zhao et al. (2005) Bioconjugate Chem. 16:758-766.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

In various embodiments, the oligomer of the invention is used in pharmaceutical formulations and compositions. Suitably, such compositions comprise a pharmaceutically acceptable diluent, carrier, salt or adjuvant. WO2007/031091 provides suitable and preferred pharmaceutically acceptable diluents, carriers and adjuvants—which are hereby incorporated by reference. Suitable dosages, formulations, administration routes, compositions, dosage forms, combinations with other therapeutic agents, pro-drug formulations are also provided in WO2007/031091—which are also hereby incorporated by reference. Details on techniques for formulation and administration also may be found in the latest edition of "REMINGTON'S PHARMACEUTICAL SCIENCES" (Maack Publishing Co, Easton Pa.).

In some embodiments, an oligomer of the invention is covalently linked to a conjugated moiety to aid in delivery of the oligomer across cell membranes. An example of a conjugated moiety that aids in delivery of the oligomer across cell membranes is a lipophilic moiety, such as cholesterol. In various embodiments, an oligomer of the invention is formulated with lipid formulations that form liposomes, such as Lipofectamine 2000 or Lipofectamine RNAiMAX, both of which are commercially available from Invitrogen. In some embodiments, the oligomers of the invention are formulated with a mixture of one or more lipid-like non-naturally occurring small molecules ("lipidoids"). Libraries of lipidoids can be synthesized by conventional synthetic chemistry methods and various amounts and combinations of lipidoids can be assayed in order to develop a vehicle for effective delivery of an oligomer of a particular size to the targeted tissue by the chosen route of administration. Suitable lipidoid libraries and compositions can be found, for example in Akinc et al. (2008) Nature Biotechnol., available at http://www.nature.com/nbt/journal/vaop/ncurrent/abs/nbt1402.html, which is incorporated by reference herein.

As used herein, the term "pharmaceutically acceptable salts" refers to salts that retain the desired biological activity of the herein identified oligomers and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylene-diamine, D-glucosamine, tetraethylammonium, or ethylenediamine; or (c) combinations of (a) and (b); e.g., a zinc tannate salt or the like.

In certain embodiments, the pharmaceutical compositions according to the invention comprise other active ingredients in addition to an oligomer or conjugate of the invention, including active agents useful for the treatment of cancer, myopathies and/or asthma.

In some embodiments, the additional active agent is selected from the group consisting of docetaxel, vincristine, 5-fluorouracil, TRAIL, irinotecan, 17-AAG, platin compounds, and irradiation.

In one embodiment, the invention provides for a combined therapy, characterised in that the therapy comprises administering the pharmaceutical composition according to the invention, and an additional active agent (e.g. docetaxel), which in certain embodiments are administered prior to, during or subsequent to the administration of the pharmaceutical compositions of the invention.

The invention also provides a kit of parts wherein a first part comprises at least one oligomer, conjugate and/or the pharmaceutical composition according to the invention and a further part comprises one or more active agents (e.g. docetaxel) useful for the treatment of cancer, myopathies and/or asthma. It is therefore envisaged that the kit of parts may be used in a method of treatment, as referred to herein, where the method comprises administering both the first part and the further part, either simultaneously or one after the other.

Applications

The term "treatment" as used herein refers to both treatment of an existing disease (e.g., a disease or disorder as referred to herein below), or prevention of a disease, i.e., prophylaxis. It will therefore be recognised that, in certain embodiments, "treatment" includes prophylaxis.

In various embodiments, the oligomers of the invention may be utilized as research reagents for, for example, diagnostics, therapeutics and prophylaxis.

In some embodiments, such oligomers may be used for research purposes to specifically inhibit the expression of Hsp27 protein (typically by degrading or inhibiting the Hsp27 mRNA and thereby preventing protein formation) in cells and experimental animals, thereby facilitating functional analysis of the target or an appraisal of its usefulness as a target for therapeutic intervention.

In certain embodiments, the oligomers may be used in diagnostics to detect and/or to quantify Hsp27 expression in cells and tissues by Northern blotting, in-situ hybridisation or similar techniques.

In various therapeutic embodiments, a non-human animal or a human suspected of having a disease or disorder which can be treated by modulating the expression of Hsp27 is treated by administering an effective amount of an oligomer in accordance with this invention. Further provided are methods of treating a mammal, such as treating a human, suspected of having or being prone to a disease or condition, associated with expression of Hsp27 by administering a therapeutically or prophylactically effective amount of one or more of the oligomers, conjugates or compositions of the invention.

In certain embodiments, the invention also provides for the use of the oligomers or conjugates of the invention as described for the manufacture of a medicament for the treatment of a disorder as referred to herein, or for a method of the treatment of a disorder as referred to herein.

In various embodiments, the invention also provides for a method for treating a disorder as referred to herein, said method comprising administering an oligomer according to the invention as herein described, and/or a conjugate according to the invention, and/or a pharmaceutical composition according to the invention to an animal in need thereof (such as a patient in need thereof).

Medical Indications

In certain therapeutic embodiments, the disorder to be treated is a hyperproliferative disorders (e.g., cancer), such as prostate cancer, lung cancer, leukemia, gastric cancer, breast cancer, ovarian cancer, bladder cancer, renal cancer, pancreatic cancer, multiple myeloma, brain tumours, fibrosarcoma osteosarcomas and liver cancer. In various embodiments, the treatment of such a disease or condition according to the invention may be combined with one or more other anti-cancer treatments, such as radiotherapy, chemotherapy or immunotherapy.

In certain other embodiments, the disorder to be treated is a myopathy and/or asthma.

In various embodiments, the disease or disorder is associated with a mutation of the Hsp27 gene or a gene whose protein product is associated with or interacts with Hsp27. Therefore, in various embodiments, the target mRNA is a mutated form of the Hsp27 sequence, for example, it comprises one or more single point mutations or triplet repeats.

In various embodiments, the disease or disorder is associated with abnormal levels of Hsp27.

The term "abnormal" as used herein refers to over-expression (e.g. up-regulation) of the Hsp27 gene in a cell compared to the expression level in a cell of an animal which does not have a disease, disorder or condition mentioned herein.

In some embodiments, an oligomer, a conjugate or a composition according to the invention can be used for the treatment of conditions associated with over-expression (e.g. up-regulation) of the Hsp27 gene.

In other embodiments, the disease or disorder is associated with abnormal levels of a mutated form of Hsp27.

The terms "mutation" and "mutated form" as used herein refer to a variant of Hsp27 nucleic acid shown in SEQ ID NO: 137. Said variant may be associated with a disease, disorder or condition as referred to herein. In some embodiments, the term "variant" as used herein refers to a nucleotide sequence having a base sequence which differs from SEQ ID NO: 137 by one or more nucleotide additions and/or substitutions and/or deletions. In some embodiments the variant has at least 80%, 85%, 90% or 95% sequence homology (identity) with SEQ ID NO: 137. In the same or different embodiment, the variant has no more that 60 additional nucleotides and/or substituted nucleotides and/or deleted nucleotides over the whole of SEQ ID NO: 137; such as no more than 30 additional nucleotides and/or substituted nucleotides and/or deleted nucleotides; such as no more that 15 additional nucleotides and/or substituted nucleotides and/or deleted nucleotides over the whole of SEQ ID NO: 137.

Hsp27 is a binding partner of numerous polypeptides. Hsp27 may act as a chaperone by binding unfolded proteins for trafficking in either refolding pathways or cellular degradation pathways. Examples of polypeptides which Hsp27 may bind to include annexin II, DAXX, F-actin, cytochrome c, caspase-3, Akt1, AR, IκBα, FAS and MDM2. In various embodiments, the invention relates to methods of modulating the expression of a gene encoding a polypeptide capable of binding to Hsp27. In other embodiments, the invention relates to methods of modulating the activity of a polypeptide capable of binding to Hsp27. In some embodiments, the binding of Hsp27 to a polypeptide results in increased expression or activity of the gene encoding the polypeptide to which Hsp27 is bound. In other embodiments, the binding of Hsp27 to a polypeptide results in decreased expression or activity of the gene encoding the polypeptide which is bound to Hsp27. In some embodiments, the binding of Hsp27 to a polypeptide results in increased activity of the polypeptide which is bound to Hsp27. In other embodiments, the binding of Hsp27 to a polypeptide results in decreased activity of the polypeptide which is bound to Hsp27.

The invention further provides use of an oligomer of the invention in the manufacture of a medicament for the treatment of any and all conditions disclosed herein.

In various embodiments, the invention is directed to a method of treating a mammal suffering from or susceptible to a condition associated with abnormal levels of Hsp27 mRNA or protein, comprising administering to the mammal a therapeutically effective amount of an oligomer of the invention, or a conjugate thereof, that comprises one or more LNA monomers.

An interesting aspect of the invention is directed to the use of an oligomer (compound) as defined herein or a conjugate as defined herein for the preparation of a medicament for the treatment of a condition as disclosed herein above.

In various embodiments, the invention encompasses a method of preventing or treating a disease comprising administering a therapeutically effective amount of an oligomer according to the invention, or a conjugate thereof, to a non-human animal or a human in need of such therapy.

In certain embodiments, the LNA oligomers of the invention, or conjugates thereof, are administered for a short period time rather than continuously.

In certain embodiments of the invention, the oligomer (compound) is linked to a conjugated moiety, for example, in order to increase the cellular uptake of the oligomer. In one embodiment the conjugated moiety is a sterol, such as cholesterol.

In various embodiments, the invention is directed to a method for treating abnormal levels of Hsp27, the method comprising administering an oligomer of the invention, or a conjugate or a pharmaceutical composition thereof, to an animal (such as a patient) in need of such treatment, and optionally further comprising the administration of a further chemotherapeutic agent. In some embodiments, the chemotherapeutic agent is conjugated to the oligomer, is present in the pharmaceutical composition, or is administered in a separate formulation.

The invention also relates to an oligomer, a composition or a conjugate as defined herein for use as a medicament.

The invention further relates to use of an oligomer, composition, or a conjugate as defined herein for the manufacture of a medicament for the treatment of abnormal levels of Hsp27 or expression of mutant forms of Hsp27 (such as allelic variants, such as those associated with one of the diseases referred to herein).

Moreover, in various embodiments, the invention relates to a method of treating an animal (such as a patient) suffering from a disease or condition selected from the group consisting of cancer, myopathies and asthma, the method comprising the step of administering a pharmaceutical composition as defined herein to the animal (such as a patient) in need thereof.

In certain embodiments, the methods of the invention are employed for treatment or prophylaxis against diseases caused by abnormal levels of Hsp27.

In some embodiments, the invention is directed to a method for treating abnormal levels of Hsp27, said method comprising administering a oligomer of the invention, or a conjugate of the invention or a pharmaceutical composition of the invention to an animal (such as a patient) in need thereof.

Moreover, the invention relates to a method of treating an animal (such as a human) suffering from a disease or condition such as those referred to herein.

An animal (such as a patient) who is in need of treatment is an animal (such as a patient) suffering from or likely to suffer from the disease or disorder.

Suitable animals include human and non-human animals. In some embodiments, the animal is a mammal. Examples include humans, rodents (such as rats and mice), rabbits, primates, non-human primates (such as chimpanzees and monkeys), horses, cattle, sheep, pigs, dogs and cats.

Suitable dosages, formulations, administration routes, compositions, dosage forms, combinations with other therapeutic agents, pro-drug formulations are also provided in WO2007/031091—which is hereby incorporated by reference.

The invention also provides for a pharmaceutical composition comprising an oligomer or a conjugate as herein described, and a pharmaceutically acceptable diluent, carrier or adjuvant. WO2007/031091 provides suitable and preferred pharmaceutically acceptable diluents, carriers and adjuvants—which are hereby incorporated by reference.

EMBODIMENTS

The following embodiments of the invention may be used in combination with the other embodiments described herein.

1. An oligomer of between 10-30 nucleotides in length which comprises a contiguous nucleotide sequence of a total of between 10-30 nucleotides, wherein said contiguous nucleotide sequence is at least 80% homologous to a region corresponding to a mammalian Hsp27 gene or the reverse complement of an mRNA, such as SEQ ID NO: 137 or a naturally occurring variant thereof.

2. The oligomer according to embodiment 1, wherein the contiguous nucleotide sequence is at least 80% homologous to a region corresponding to any of SEQ ID NO: 1-15 and 121, 16-30 and 122, 31-45 and 123, 46-60 and 124, 61-75 and 125, 76-90 and 126, 91-105, and 127, and 106-120 and 128.

3. The oligomer according to embodiment 1 or 2, wherein the contiguous nucleotide sequence comprises no mismatches or no more than one or two mismatches with the reverse complement of the corresponding region of 137.

4. The oligomer according to any one of embodiments 1 to 3, wherein the nucleotide sequence of the oligomer consists of the contiguous nucleotide sequence.

5. The oligomer according to any one of embodiments 1 to 4, wherein the contiguous nucleotide sequence is between 10-18 nucleotides in length.

6. The oligomer according to any one of embodiments 1 to 5, wherein the contiguous nucleotide sequence comprises nucleotide analogues.

7. The oligomer according to embodiment 6, wherein the nucleotide analogues are sugar modified nucleotides, such as sugar modified nucleotides selected from the group consisting of: Locked Nucleic Acid (LNA) units; 2'-O-alkyl-RNA units, 2'-OMe-RNA units, 2'-amino-DNA units, and 2'-fluoro-DNA units.
8. The oligomer according to embodiment 6, wherein the nucleotide analogues are LNA.
9. The oligomer according to any one of embodiments 6 to 8 which is a gapmer.
10. The oligomer according to any one of embodiments 1 to 9, which inhibits the expression of Hsp27 gene or mRNA in a cell which is expressing Hsp27 gene or mRNA.
11. The oligomer according to any one of embodiments 1 to 10 which is selected from the group consisting of SEQ ID NO 129, 130, 131, 132, 133, 134, 135 and 136.
12. A conjugate comprising the oligomer according to any one of embodiments 1 to 11, and at least one non-nucleotide or non-polynucleotide moiety covalently attached to said oligomer.
13. A pharmaceutical composition comprising the oligomer according to any one of embodiments 1 to 10, or the conjugate according to embodiment 12, and a pharmaceutically acceptable diluent, carrier, salt or adjuvant.
14. The oligomer according to any one of embodiments 1 to 11, or the conjugate according to embodiment 12, for use as a medicament, such as for the treatment of cancer, myopathies and asthma.
15. The use of an oligomer according to any one of the embodiments 1 to 11, or a conjugate as defined in embodiment 12, for the manufacture of a medicament for the treatment of cancer, myopathies and asthma.
16. A method of treating cancer, myopathies and asthma, said method comprising administering an oligomer according to any one of embodiments 1 to 11, or a conjugate according to embodiment 12, or a pharmaceutical composition according to embodiment 13, to a patient suffering from, or likely to suffer from cancer, myopathies and asthma.
17. A method for the inhibition of Hsp27 in a cell which is expressing Hsp27, said method comprising administering an oligomer according to any one of the embodiments 1 to 11, or a conjugate according to embodiment 12 to said cell so as to inhibit Hsp27 in said cell.

EXAMPLES

Example 1

Monomer Synthesis

The LNA monomer building blocks and derivatives were prepared following published procedures and references cited therein—see WO07/031,081 and the references cited therein.

Example 2

Oligonucleotide Synthesis

Oligonucleotides (oligomers) were synthesized according to the method described in WO07/031,081. Table 1 shows examples of antisense oligonucleotide motifs and of the invention.

Example 3

Design of the Oligonucleotides

In accordance with the invention, a series of oligonucleotides (oligomers) were designed to target different regions of the human Hsp27 mRNA using the published sequence GenBank accession number NM_001540, presented herein as SEQ ID NO: 137 (FIG. 3)

TABLE 1

Antisense oligonucleotide sequences of the invention. SEQ ID NOS: 1-120 and SEQ ID NOS: 121-128 (shown in Table 2) are oligomer sequences designed to target human Hsp27 mRNA.

| SEQ ID NO | Sequence (5'-3') | Length (bases) |
|---|---|---|
| SEQ ID NO: 1 | GAGATGTAGCCATGCT | 16 |
| SEQ ID NO: 2 | GAGATGTAGCCATGC | 15 |
| SEQ ID NO: 3 | AGATGTAGCCATGCT | 15 |
| SEQ ID NO: 4 | GAGATGTAGCCATG | 14 |
| SEQ ID NO: 5 | AGATGTAGCCATGC | 14 |
| SEQ ID NO: 6 | GATGTAGCCATGCT | 14 |
| SEQ ID NO: 7 | GAGATGTAGCCAT | 13 |
| SEQ ID NO: 8 | AGATGTAGCCATG | 13 |
| SEQ ID NO: 9 | GATGTAGCCATGC | 13 |
| SEQ ID NO: 10 | ATGTAGCCATGCT | 13 |
| SEQ ID NO: 11 | GAGATGTAGCCA | 12 |
| SEQ ID NO: 12 | AGATGTAGCCAT | 12 |
| SEQ ID NO: 13 | GATGTAGCCATG | 12 |
| SEQ ID NO: 14 | ATGTAGCCATGC | 12 |
| SEQ ID NO: 15 | TGTAGCCATGCT | 12 |
| SEQ ID NO: 16 | ACGGTCAGTGTGCCCT | 16 |
| SEQ ID NO: 17 | ACGGTCAGTGTGCCC | 15 |
| SEQ ID NO: 18 | CGGTCAGTGTGCCCT | 15 |
| SEQ ID NO: 19 | ACGGTCAGTGTGCC | 14 |
| SEQ ID NO: 20 | CGGTCAGTGTGCCC | 14 |
| SEQ ID NO: 21 | GGTCAGTGTGCCCT | 14 |
| SEQ ID NO: 22 | GTCAGTGTGCCCT | 13 |
| SEQ ID NO: 23 | GGTCAGTGTGCCC | 13 |
| SEQ ID NO: 24 | CGGTCAGTGTGCC | 13 |
| SEQ ID NO: 25 | ACGGTCAGTGTGC | 13 |
| SEQ ID NO: 26 | ACGGTCAGTGTG | 12 |
| SEQ ID NO: 27 | CGGTCAGTGTGC | 12 |
| SEQ ID NO: 28 | GGTCAGTGTGCC | 12 |
| SEQ ID NO: 29 | GTCAGTGTGCCC | 12 |
| SEQ ID NO: 30 | TCAGTGTGCCCT | 12 |
| SEQ ID NO: 31 | CGTGTATTTCCGCGTG | 16 |
| SEQ ID NO: 32 | CGTGTATTTCCGCGT | 15 |
| SEQ ID NO: 33 | GTGTATTTCCGCGTG | 15 |
| SEQ ID NO: 34 | CGTGTATTTCCGCG | 14 |

TABLE 1-continued

Antisense oligonucleotide sequences of the invention. SEQ ID NOS: 1-120 and SEQ ID NOS: 121-128 (shown in Table 2) are oligomer sequences designed to target human Hsp27 mRNA.

| SEQ ID NO | Sequence (5'-3') | Length (bases) |
|---|---|---|
| SEQ ID NO: 35 | GTGTATTTCCGCGT | 14 |
| SEQ ID NO: 36 | TGTATTTCCGCGTG | 14 |
| SEQ ID NO: 37 | CGTGTATTTCCGC | 13 |
| SEQ ID NO: 38 | GTGTATTTCCGCG | 13 |
| SEQ ID NO: 39 | TGTATTTCCGCGT | 13 |
| SEQ ID NO: 40 | GTATTTCCGCGTG | 13 |
| SEQ ID NO: 41 | CGTGTATTTCCG | 12 |
| SEQ ID NO: 42 | GTGTATTTCCGC | 12 |
| SEQ ID NO: 43 | TGTATTTCCGCG | 12 |
| SEQ ID NO: 44 | GTATTTCCGCGT | 12 |
| SEQ ID NO: 45 | TATTTCCGCGTG | 12 |
| SEQ ID NO: 46 | TGCGTGGCTAGCTTGG | 16 |
| SEQ ID NO: 47 | TGCGTGGCTAGCTTG | 15 |
| SEQ ID NO: 48 | GCGTGGCTAGCTTGG | 15 |
| SEQ ID NO: 49 | TGCGTGGCTAGCTT | 14 |
| SEQ ID NO: 50 | GCGTGGCTAGCTTG | 14 |
| SEQ ID NO: 51 | CGTGGCTAGCTTGG | 14 |
| SEQ ID NO: 52 | TGCGTGGCTAGCT | 13 |
| SEQ ID NO: 53 | GCGTGGCTAGCTT | 13 |
| SEQ ID NO: 54 | CGTGGCTAGCTTG | 13 |
| SEQ ID NO: 55 | GTGGCTAGCTTGG | 13 |
| SEQ ID NO: 56 | TGCGTGGCTAGC | 12 |
| SEQ ID NO: 57 | GCGTGGCTAGCT | 12 |
| SEQ ID NO: 58 | CGTGGCTAGCTT | 12 |
| SEQ ID NO: 59 | GTGGCTAGCTTG | 12 |
| SEQ ID NO: 60 | TGGCTAGCTTGG | 12 |
| SEQ ID NO: 61 | ATGGTGATCTCGTTGG | 16 |
| SEQ ID NO: 62 | ATGGTGATCTCGTTG | 15 |
| SEQ ID NO: 63 | TGGTGATCTCGTTGG | 15 |
| SEQ ID NO: 64 | ATGGTGATCTCGTT | 14 |
| SEQ ID NO: 65 | TGGTGATCTCGTTG | 14 |
| SEQ ID NO: 66 | GGTGATCTCGTTGG | 14 |
| SEQ ID NO: 67 | ATGGTGATCTCGT | 13 |
| SEQ ID NO: 68 | TGGTGATCTCGTT | 13 |
| SEQ ID NO: 69 | GGTGATCTCGTTG | 13 |
| SEQ ID NO: 70 | GTGATCTCGTTGG | 13 |
| SEQ ID NO: 71 | ATGGTGATCTCG | 12 |
| SEQ ID NO: 72 | TGGTGATCTCGT | 12 |
| SEQ ID NO: 73 | GGTGATCTCGTT | 12 |
| SEQ ID NO: 74 | GTGATCTCGTTG | 12 |
| SEQ ID NO: 75 | TGATCTCGTTGG | 12 |
| SEQ ID NO: 76 | ATTTTGCAGCTTCTGG | 16 |
| SEQ ID NO: 77 | ATTTTGCAGCTTCTG | 15 |
| SEQ ID NO: 78 | TTTTGCAGCTTCTGG | 15 |
| SEQ ID NO: 79 | ATTTTGCAGCTTCT | 14 |
| SEQ ID NO: 80 | TTTTGCAGCTTCTG | 14 |
| SEQ ID NO: 81 | TTTGCAGCTTCTGG | 14 |
| SEQ ID NO: 82 | ATTTTGCAGCTTC | 13 |
| SEQ ID NO: 83 | TTTTGCAGCTTCT | 13 |
| SEQ ID NO: 84 | TTTGCAGCTTCTG | 13 |
| SEQ ID NO: 85 | TTGCAGCTTCTGG | 13 |
| SEQ ID NO: 86 | ATTTTGCAGCTT | 12 |
| SEQ ID NO: 87 | TTTTGCAGCTTC | 12 |
| SEQ ID NO: 88 | TTTGCAGCTTCT | 12 |
| SEQ ID NO: 89 | TTGCAGCTTCTG | 12 |
| SEQ ID NO: 90 | TGCAGCTTCTGG | 12 |
| SEQ ID NO: 91 | GGCACAGCCAGTGGCG | 16 |
| SEQ ID NO: 92 | GGCACAGCCAGTGGC | 15 |
| SEQ ID NO: 93 | GCACAGCCAGTGGCG | 15 |
| SEQ ID NO: 94 | GGCACAGCCAGTGG | 14 |
| SEQ ID NO: 95 | GCACAGCCAGTGGC | 14 |
| SEQ ID NO: 96 | CACAGCCAGTGGCG | 14 |
| SEQ ID NO: 97 | GGCACAGCCAGTG | 13 |
| SEQ ID NO: 98 | GCACAGCCAGTGG | 13 |
| SEQ ID NO: 99 | CACAGCCAGTGGC | 13 |
| SEQ ID NO: 100 | ACAGCCAGTGGCG | 13 |
| SEQ ID NO: 101 | GGCACAGCCAGT | 12 |
| SEQ ID NO: 102 | GCACAGCCAGTG | 12 |
| SEQ ID NO: 103 | CACAGCCAGTGG | 12 |
| SEQ ID NO: 104 | ACAGCCAGTGGC | 12 |
| SEQ ID NO: 105 | CAGCCAGTGGCG | 12 |
| SEQ ID NO: 106 | TATCAAAAGAACACAC | 16 |

TABLE 1-continued

Antisense oligonucleotide sequences of the invention. SEQ ID NOS: 1-120 and SEQ ID NOS: 121-128 (shown in Table 2) are oligomer sequences designed to target human Hsp27 mRNA.

| SEQ ID NO | Sequence (5'-3') | Length (bases) |
|---|---|---|
| SEQ ID NO: 107 | TATCAAAAGAACACA | 15 |
| SEQ ID NO: 108 | ATCAAAAGAACACAC | 15 |
| SEQ ID NO: 109 | TATCAAAAGAACAC | 14 |
| SEQ ID NO: 110 | ATCAAAAGAACACA | 14 |
| SEQ ID NO: 111 | TCAAAAGAACACAC | 14 |
| SEQ ID NO: 112 | TATCAAAAGAACA | 13 |
| SEQ ID NO: 113 | ATCAAAAGAACAC | 13 |
| SEQ ID NO: 114 | TCAAAAGAACACA | 13 |
| SEQ ID NO: 115 | CAAAAGAACACAC | 13 |
| SEQ ID NO: 116 | TATCAAAAGAAC | 12 |
| SEQ ID NO: 117 | ATCAAAAGAACA | 12 |
| SEQ ID NO: 118 | TCAAAAGAACAC | 12 |
| SEQ ID NO: 119 | CAAAAGAACACA | 12 |
| SEQ ID NO: 120 | AAAAGAACACAC | 12 |

Table 2 shows 24mer sequence motifs from which oligomers of the invention may be designed—the bold type represents 16mer sequence motifs as shown in Table 1.

TABLE 2

24mers Sequence motifs

| 16mer SEQ IDs | Corresponding 24mer sequence comprising 16mer | 24mer SEQ ID |
|---|---|---|
| SEQ ID NO: 1 | ccgggagatgtagccatgctcgtc | SEQ ID NO: 121 |
| SEQ ID NO: 16 | ctccacggtgcagtgtgccctcagg | SEQ ID NO: 122 |
| SEQ ID NO: 31 | gcagcgtgtatttccgcgtgaagc | SEQ ID NO: 123 |
| SEQ ID NO: 46 | ggactgcgtggctagcttgggcat | SEQ ID NO: 124 |
| SEQ ID NO: 61 | tgggatggtgatctcgttggactg | SEQ ID NO: 125 |
| SEQ ID NO: 76 | tcggattttgcagcttctgggccc | SEQ ID NO: 126 |
| SEQ ID NO: 91 | gggaggcacagccagtggcggcag | SEQ ID NO: 127 |
| SEQ ID NO: 106 | aatgtatcaaaagaacacacaggt | SEQ ID NO: 128 |

Table 3: Oligonucleotide Designs of the Invention

In SEQ ID NOs: 129-136, upper case letters indicates nucleotide (nucleoside) analogue monomers (e.g. β-D-oxy LNA monomers) and subscript "s" represents phosphorothioate linkage groups between the monomers. In some embodiments, all cytosine bases in LNA monomers are 5-methylcytosines. Lower case letters represent nucleotide (DNA) monomers. "s" may be substituted with any other internucleoside linkage, such as those described herein.

TABLE 3

Oligomer designs

| SEQ ID NO | Sequence (5'-3') |
|---|---|
| SEQ ID NO: 129 | G$_s$A$_s$G$_s$a$_s$t$_s$g$_s$t$_s$a$_s$g$_s$c$_s$c$_s$a$_s$t$_s$G$_s$C$_s$T |
| SEQ ID NO: 130 | A$_s$C$_s$G$_s$g$_s$t$_s$c$_s$a$_s$g$_s$t$_s$g$_s$t$_s$g$_s$c$_s$C$_s$C$_s$T |
| SEQ ID NO: 131 | C$_s$G$_s$T$_s$g$_s$t$_s$a$_s$t$_s$t$_s$t$_s$c$_s$c$_s$g$_s$c$_s$G$_s$T$_s$G |
| SEQ ID NO: 132 | T$_s$G$_s$C$_s$g$_s$t$_s$g$_s$g$_s$c$_s$t$_s$a$_s$g$_s$c$_s$t$_s$T$_s$G$_s$G |
| SEQ ID NO: 133 | A$_s$T$_s$G$_s$g$_s$t$_s$g$_s$a$_s$t$_s$c$_s$t$_s$c$_s$g$_s$t$_s$T$_s$G$_s$G |
| SEQ ID NO: 134 | A$_s$T$_s$T$_s$t$_s$t$_s$g$_s$c$_s$a$_s$g$_s$c$_s$t$_s$t$_s$c$_s$T$_s$G$_s$G |
| SEQ ID NO: 135 | G$_s$G$_s$C$_s$a$_s$c$_s$a$_s$g$_s$c$_s$c$_s$a$_s$g$_s$t$_s$g$_s$G$_s$C$_s$G |
| SEQ ID NO: 136 | T$_s$A$_s$T$_s$c$_s$a$_s$a$_s$a$_s$a$_s$g$_s$a$_s$a$_s$c$_s$a$_s$C$_s$A$_s$C |

Example 4

In Vitro Model: Cell Culture

The effect of antisense oligonucleotides on target nucleic acid expression can be tested in any of a variety of cell types provided that the target nucleic acid is present at measurable levels. The target can be expressed endogenously or by transient or stable transfection of a nucleic acid encoding said target nucleic acid. The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen. Cells were cultured in the appropriate medium as described below and maintained at 37° C. at 95-98% humidity and 5% CO$_2$. Cells were routinely passaged 2-3 times weekly.

A549 The human lung cancer cell line A549 was cultured in DMEM (Sigma)+10% fetal bovine serum (FBS)+2 mM Glutamax I+gentamicin (25 µg/ml).

PC3 The human prostate cancer cell line PC3 was cultured in DMEM (Sigma)+10% fetal bovine serum (FBS)+2 mM Glutamax I+gentamicin (25 µg/ml).

Example 5

In Vitro Model: Treatment with Antisense Oligonucleotide

The cells were treated with an oligomer (oligonucleotide) using the cationic liposome formulation LipofectAMINE 2000 (Gibco) as transfection vehicle. Cells were seeded in 6-well cell culture plates (NUNC) and treated when 75-90% confluent. Oligonucleotide concentrations used ranged from 1 nM to 16 nM final concentration. Formulation of oligonucleotide-lipid complexes were carried out essentially as described by the manufacturer using serum-free OptiMEM (Gibco) and a final lipid concentration of 5 µg/mL LipofectAMINE 2000. Cells were incubated at 37° C. for 4 hours and treatment was stopped by removal of oligonucleotide-containing culture medium. Cells were washed and serum-containing media was added. After oligonucleotide treatment, cells were allowed to recover for 20 hours before they were harvested for RNA analysis.

Example 6

In Vitro Model: Extraction of RNA and cDNA Synthesis

For RNA isolation from the cell lines, the RNeasy mini kit (Qiagen cat. no. 74104) was used according to the protocol provided by the manufacturer. First strand synthesis was performed using Reverse Transcriptase reagents from Ambion according to the manufacturer's instructions.

For each sample, 0.5·g total RNA was adjusted to 10.8·l with RNase free H$_2$O and mixed with 2·l random decamers (50·M) and 4·l dNTP mix (2.5 mM each dNTP) and heated to 70° C. for 3 min after which the samples were rapidly cooled on ice. After cooling the samples on ice, 2·l 10×Buffer RT, 1·l MMLV Reverse Transcriptase (100 U/·l) and 0.25·l RNase inhibitor (10 U/·l) was added to each sample, followed by incubation at 42° C. for 60 min, heat inactivation of the enzyme at 95° C. for 10 min and then the sample was cooled to 4° C.

Example 7

In Vitro Model: Analysis of Oligonucleotide Inhibition of Hsp27 Expression by Real-Time PCR Antisense modulation of Hsp27 mRNA expression can be assayed in a variety of ways known in the art. For example, Hsp27 mRNA levels can be quantitated by, e.g., Northern blot analysis, competitive polymerase chain reaction (PCR), or real-time quantitative PCR. Real-time quantitative PCR is presently preferred. RNA analysis can be performed on total cellular RNA or mRNA. Methods of RNA isolation and RNA analysis such as Northern blot analysis is routine in the art and is taught in, for example, Current Protocols in Molecular Biology, John Wiley and Sons. Real-time quantitative (PCR) can be conveniently accomplished using the commercially available Multi-Color Real Time PCR Detection System, available from Applied Biosystem.

Real-Time Quantitative PCR Analysis of Hsp27 mRNA Levels

The content of human Hsp27 mRNA in the samples was quantified using the human Hsp27 ABI Prism Pre-Developed TaqMan Assay Reagent (Applied Biosystems cat. no. Hs03044127_g1) according to the manufacturer's instructions. Glyceraldehyde-3-phosphate dehydrogenase (GAPDH) mRNA quantity was used as an endogenous control for normalizing any variance in sample preparation. The sample content of human GAPDH mRNA was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example Heid et al. Real time quantitative PCR, Genome Research (1996), 6: 986-994.

Real Time PCR

The cDNA from the first strand synthesis performed as described in Example 6 was diluted 2-20 times, and analyzed by real time quantitative PCR using Taqman 7500 FAST from Applied Biosystems. The primers and probe were mixed with 2× Taqman Fast Universal PCR master mix (2×) (Applied Biosystems Cat. #4364103) and added to 4 µl cDNA to a final volume of 10 µl. Each sample was analysed in triplicate. Standard curves were generated by assaying 2-fold dilutions of a cDNA that had been prepared on material purified from a cell line expressing the RNA of interest. Sterile H$_2$O was used instead of cDNA for the no template control. PCR program: 95° C. for 30 seconds, followed by 40 cycles of 95° C., 3 seconds, 60° C., 30 seconds. Relative quantities of target mRNA sequence were determined from the calculated Threshold cycle using the Applied Biosystems Fast System SDS Software Version 1.3.1.21.

Example 8

In Vitro Analysis: Antisense Inhibition of Human Hsp27 Expression by Oligonucleotides Oligonucleotides presented in Table 4 were evaluated for their potential to knockdown Hsp27 mRNA expression at concentrations of 1, 4 and 16 nM in PC3 cells (see FIG. 1). The data are presented in Table 4 as percentage down-regulation of Hsp27 mRNA relative to mock transfected cells at 4 nM. Mock transfected cells are transfected with lipid, but without oligo (a negative control). Lower case letters represent DNA units, bold upper case letters represent LNA such as β-D-oxy-LNA units. All cytosine bases in the LNA monomers are 5-methylcytosine. Subscript "s" represents phosphorothioate linkage.

TABLE 4

| Specific Compound SEQ ID | Oligomer SEQ ID NO: | Sequence (5'-3') | Hsp27 mRNA (% inhib.) |
|---|---|---|---|
| SEQ ID NO: 138 | SEQ ID NO: 129 | G$_s$A$_s$G$_s$a$_s$t$_s$g$_s$t$_s$a$_s$g$_s$c$_s$c$_s$a$_s$t$_s$G$_s$C$_s$T | 78% |
| SEQ ID NO: 139 | SEQ ID NO: 130 | A$_s$C$_s$G$_s$g$_s$t$_s$c$_s$a$_s$g$_s$t$_s$g$_s$t$_s$g$_s$c$_s$C$_s$C$_s$T | 79% |
| SEQ ID NO: 140 | SEQ ID NO: 131 | C$_s$G$_s$T$_s$g$_s$t$_s$a$_s$t$_s$t$_s$t$_s$c$_s$c$_s$c$_s$g$_s$c$_s$G$_s$T$_s$G | 78% |

TABLE 4-continued

| Specific Compound SEQ ID | Oligomer SEQ ID NO: | Sequence (5'-3') | Hsp27 mRNA (% inhib.) |
|---|---|---|---|
| SEQ ID NO: 141 | SEQ ID NO: 132 | T$_s$G$_s$C$_s$g$_s$t$_s$g$_s$g$_s$c$_s$t$_s$a$_s$g$_s$c$_s$t$_s$T$_s$G$_s$G | 93% |
| SEQ ID NO: 142 | SEQ ID NO: 133 | A$_s$T$_s$G$_s$g$_s$t$_s$g$_s$a$_s$t$_s$c$_s$t$_s$g$_s$c$_s$t$_s$T$_s$G$_s$G | 79% |
| SEQ ID NO: 143 | SEQ ID NO: 134 | A$_s$T$_s$T$_s$t$_s$t$_s$g$_s$c$_s$a$_s$g$_s$c$_s$t$_s$t$_s$c$_s$T$_s$G$_s$G | 79% |
| SEQ ID NO: 144 | SEQ ID NO: 135 | G$_s$G$_s$C$_s$a$_s$c$_s$a$_s$g$_s$c$_s$c$_s$a$_s$g$_s$t$_s$g$_s$G$_s$C$_s$G | 94% |
| SEQ ID NO: 145 | SEQ ID NO: 136 | T$_s$A$_s$T$_s$c$_s$a$_s$a$_s$a$_s$a$_s$g$_s$a$_s$a$_s$c$_s$a$_s$C$_s$A$_s$C | 78% |

As shown in Table 4, oligonucleotides of SEQ ID NOs: 129, 130, 131, 132, 133, 134, 135 and 136 demonstrated about 75% or greater inhibition of Hsp27 mRNA expression at 4 nM in these experiments and are therefore preferred. Also preferred are oligonucleotides based on the illustrated antisense oligonucleotide sequences, for example varying the length (shorter or longer) and/or nucleobase content (e.g. the type and/or proportion of analogue units), which also provide good inhibition of Hsp27 mRNA expression.

Example 9

Measurement of Proliferating Viable Cells (MTS Assay)

PC3 cells were seeded to a density of 200,000 cells per well in a 6 well plate in 2 ml medium DMEM (Sigma D5671)+2 mM Glutamax I (Gibco 35050-038)+10% FBS (Brochrom #193575010)+25 μg/μl Gentamicin (Sigma G1397 50 mg/ml) the day prior to transfection. The next day cells were transfected as described in Example 5. The final oligonucleotide concentrations were 4 and 16 nM. After 4 hours of treatment, media was removed and cells were trypsinized and seeded to a density of 5000 cells per well in clear 96 well plates (Scientific Orange no. 1472030100) in 100 μA DMEM medium (Sigma D5671)+2 mM Glutamax I (Gibco 35050-038)+10% FBS (Brochrom #193575010)+25 μg/μl Gentamicin (Sigma G1397 50 mg/ml). Viable cells were measured at the times indicated by adding 10 μl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (CellTiter 96® AQueous One Solution Cell Proliferation Assay, Promega). Viable cells were measured at 490 nm in a Powerwave (Biotek Instruments). The OD490 nm was plotted against time/h. (See FIG. 2).

Example 10

Preparation of a Conjugate of SEQ ID NO: 129, 130, 131, 132, 133, 134, 135 and 136 and Polyethylene Glycol An oligomer is functionalized on the 5' terminus by attaching an aminoalkyl group, such as hexan-1-amine blocked with a blocking group such as Fmoc to the 5' phosphate group of the oligomer using routine phosphoramidite chemistry, oxidizing the resultant compound, deprotecting it and purifying it to achieve the functionalized oligomer (an activated oligomer) having the formula (I):

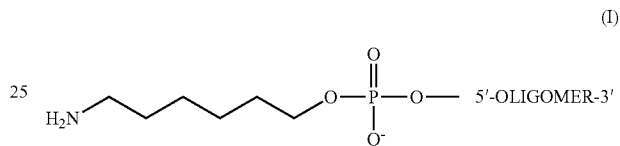

The term oligomer in formula (I) or (III) refers to an oligomer of the invention—such as an oligomer selected from the group consisting of SEQ ID NO: 129, 130, 131, 132, 133, 134, 135 and 136.

A solution of activated PEG, such as the one shown in formula (II):

(II)

wherein the PEG moiety has an average molecular weight of 12,000, and the compound of formula (I) in PBS buffer is stirred at room temperature for 12 hours. The reaction solution is extracted three times with methylene chloride and the combined organic layers are dried over magnesium sulphate and filtered and the solvent is evaporated under reduced pressure. The residue is dissolved in double distilled water and loaded onto an anion exchange column. Unreacted PEG linker is eluted with water and the product is eluted with NH$_4$HCO$_3$ solution. Fractions containing pure product are pooled and lyophilized to yield the conjugate of formula (III):

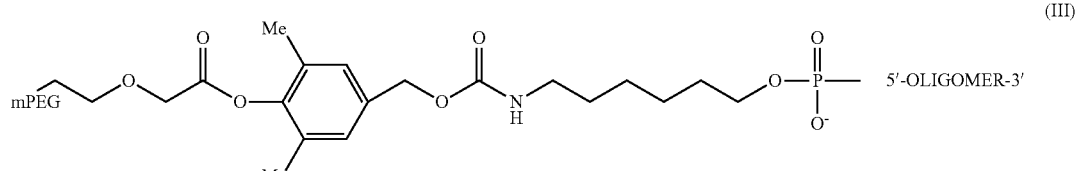

(III)

wherein the oligomer (for example, SEQ ID NO: 129, 130, 131, 132, 133, 134, 135 and 136) is attached to a PEG polymer having average molecular weight of 12,000 via a releasable linker.

Example 11

IC$_{50}$ Determination

Figure 4:
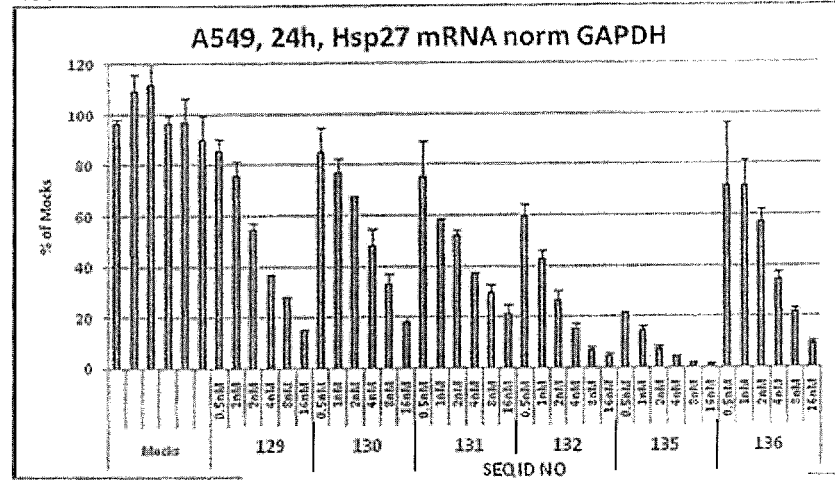
FIG. 4. $IC_{50}$ determination of oligomers in A549 cells. QPCR data from A549 cells 24 h after transfection with Hsp27 oligomers (which may be referred to as oligos). The data have been normalized with GAPDH mRNA expression and are compared to target expression in mock (100%). Mock transfected cells are transfected with the transfection agent only (negative control).
Figure 5:
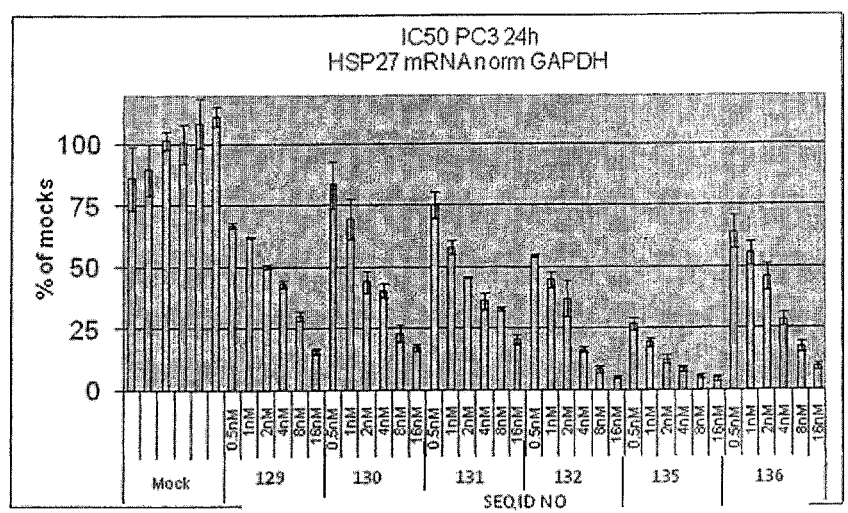
FIG. 5. $IC_{50}$ determination of oligomers in PC3 cells. QPCR data from PC3 cells 24 h after transfection with Hsp27 oligos. The data have been normalized with GAPDH mRNA expression and are compared to target expression in mock (100%). Mock transfected cells are transfected with the transfection agent only (negative control).

The experimental procedure used is as described above in Examples 4, 5, 6 and 7. All six Hsp27 oligomers (oligos) tested have IC$_{50}$·4 nM in both cell lines A549 (FIG. 4) and PC3 (FIG. 5).

Example 12

Plasma Stability

Figure 6:
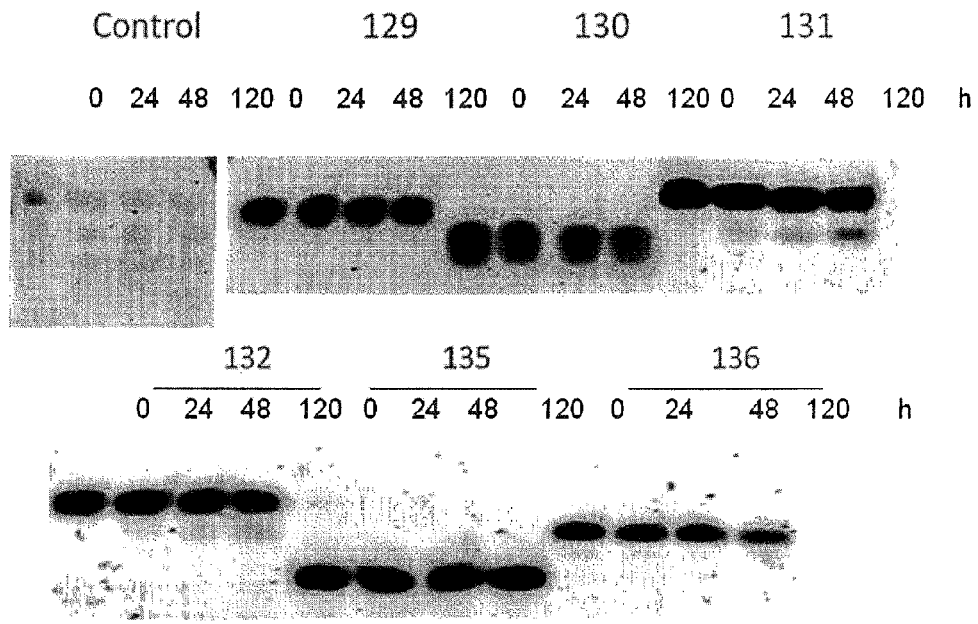
FIG. 6. Serum stability assay-digestion at 37° C. with aliquots taken at 0, 24, 48 and 120 h. The results are visualized by gel electrophoresis in PAGE. A DNA phosphorothioate has been used as a positive control.

The stability of the Hsp27 oligomers was investigated after incubation in mouse plasma at 37° C. for 24 h (1 day), 48 h (two days) and 120 h (five days). All oligomers showed in-vitro stability whereby more than 90% of active compound remained after 24 h when incubated with mouse plasma at 37° C. h. For oligomers 131 and 132, a weaker band appeared after 24-48 h, which became especially prominent after 120 h. Methodology: Mouse plasma (Lithium heparin plasma from BomTac:NMRI mice, collected 14-09-05, Taconic Europe) was defrosted and aliquoted into tubes with 45·l plasma/tube. Following, 5·l oligomer (200·M) was added to the 45·l plasma to a final concentration of 20·M. After thorough mixing, the samples were incubated at 37° C. for 0-120 hrs. At different time points (Oh, 24 h, 48 h and 120 h) samples were collected and the reaction was quenched by snap freezing the samples in liquid nitrogen. For analysis, samples were added to loading buffer and analysed by electrophoresis on a PAGE-sequencing gel under denaturing conditions. The results are shown in FIG. 6.

Example 13

T$_m$ Determination

The melting temperature of the LNA-containing oligomer/RNA duplexes was determined using a UV-spectrometry system with corresponding software (Perkin Elmer, Fremont, USA). The LNA oligomer and its complementary RNA were added in final concentrations of 1.5·M to the T$_m$-buffer (200 nM NaCl, 0.2 nM EDTA, 20 mM NaP, pH 7.0). Duplex formation was prepared by heating the samples to 95° C. for 3 min followed by cooling at room temperature for 30 min. Melting temperature (T$_m$) values were measured in a Lambda 25 UV/VIS spectrometer (Perkin Elmer) and data were collected and analysed using the TempLab software (Perkin Elmer). The instrument was programmed to heat the oligomer duplex sample from 20-95° C. and afterwards cooling the sample to 25° C. During this process the absorbance at 260 nm was recorded. The melting curves were used to calculate T$_m$ values. The T$_m$'s of the oligomers against RNA were determined (Table 5). SEQ IDs 129, 130, 131, 132 and 135 have T$_m$'s around 70° C. SEQ ID No 136 has a T$_m$ of 44.4° C.

TABLE 5

| Tm determination against complementary RNA. | |
|---|---|
| Oligo | Tm/RNA ° C. |
| 129 | 67.6° C. |
| 130 | 78.1° C. |
| 131 | 68.1° C. |
| 132 | 73.8° C. |
| 135 | 76.4° C. |
| 136 | 44.4° C. |

Example 14

Figure 7:
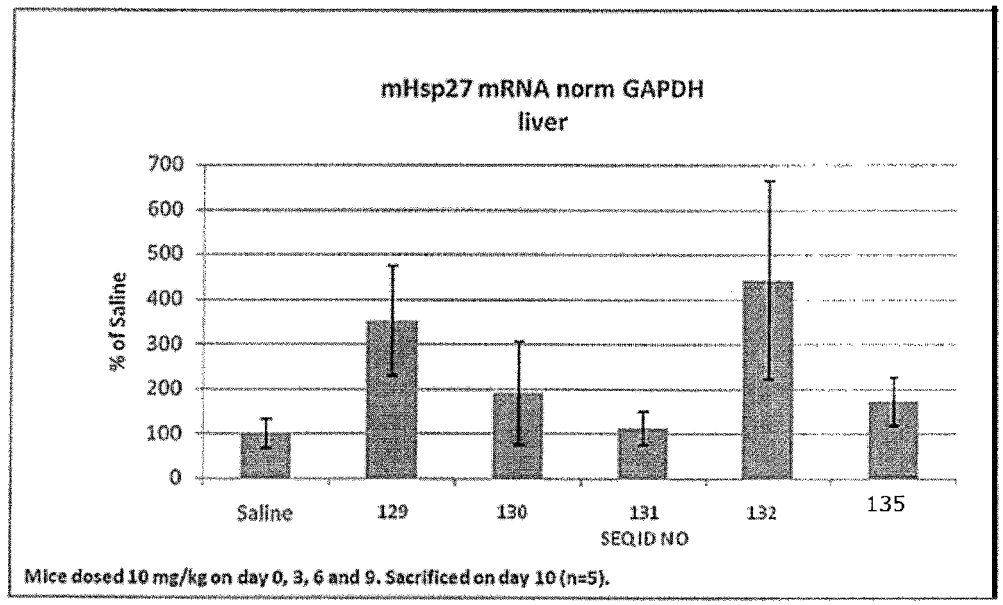
FIG. 7. Hsp27 mRNA down-regulation in mouse liver of mice treated with Hsp27 oligomers.

In Vivo Analysis: Down-Regulation of Mouse Hsp27 in Mouse Liver after in Vivo (i.v.) Administration of HSP27 Oligonucleotides Female NMRI mice received i.v. injection of oligonucleotides having the sequences of SEQ ID NO: 129, 130, 131, 132 and 135 on three consecutive days at a dosage of 25 mg/kg. Animals were sacrificed 24 h after last dosing. The liver was stored in RNA/ater stabilizing solution until use. Total RNA was extracted from liver tissue and Hsp27 mRNA levels were analyzed with qPCR (quantitative PCR). Data were compared to Hsp27 expression in saline treated control animals. The results are shown in FIG. 7.

Example 15

Figure 8:
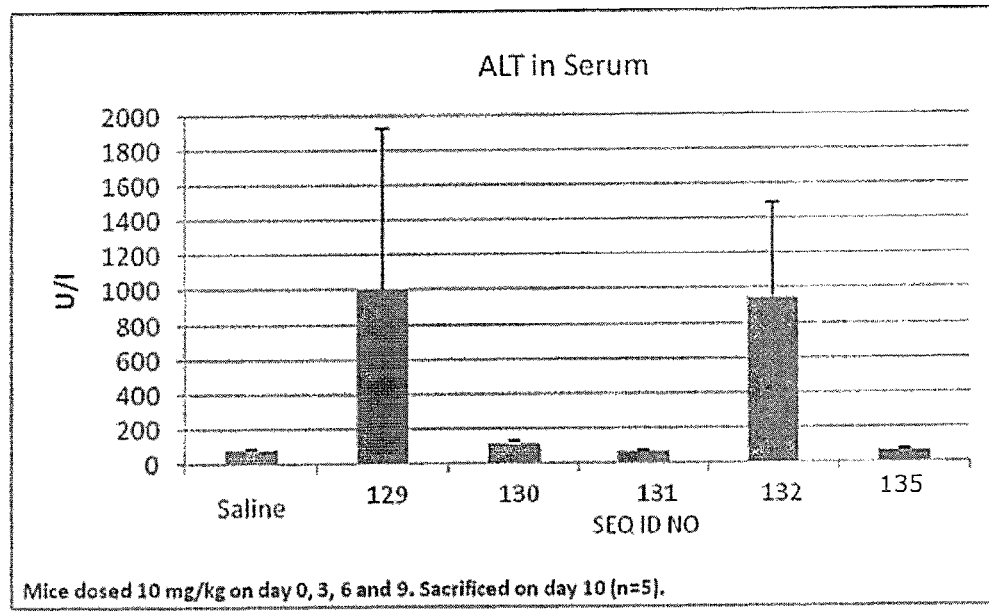
FIG. 8. ALT levels in mouse blood serum in mice treated with Hsp27 oligomers.
Figure 9:
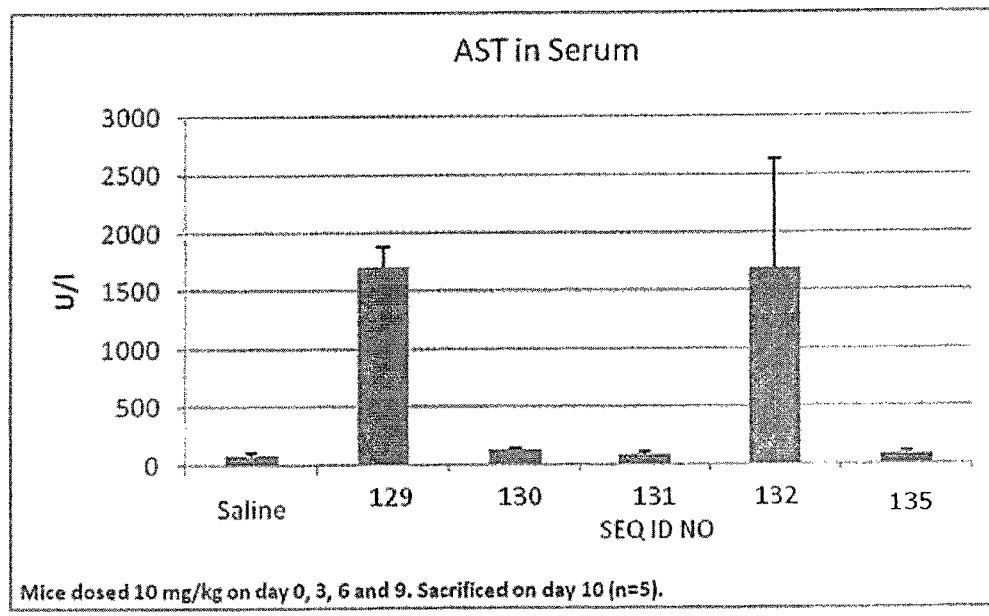
FIG. 9. AST levels in mouse blood serum in mice treated with Hsp27 oligomers.

In Vivo Analysis: ALT and AST Determination in Mouse Liver after I.V. Administration of HSP27 Oligonucleotides Female NMRI mice received i.v. injection of oligonucleotides having the sequences of SEQ ID NO: 129, 130, 131, 132 and 135 on day 0, 3, 6 and 9 at a dosage of 10 mg/kg. Animals were sacrificed 24 h after last dosing. ALT and AST levels were determined in the blood serum, free from red blood cells, obtained from the mice at the time of sacrifice. The activity of alanine-aminotransferase (ALT) and aspartate-aminotransferase (AST) in mouse serum was determined using an enzymatic ALT assay (ABX Pentra A11A01627 (ALT) or A11A01629 (AST), Horiba ABX Diagnostics, France) according to the manufacturer's instruction but adjusted to 96-well format. In short, serum samples were diluted 2.5 fold with H$_2$O and assayed in duplicate. After addition of 50 µl diluted sample or standard (multical from ABX Pentra, A11A01652) to each well, 200 µl of 37° C. ALT reagent mix was added to each well. Kinetic measurements were performed at 340 nm and 37° C. for 5 min with an interval of 30s. Data were correlated to the 2-fold diluted standard curve and results were presented as ALT activity in U/L. The results are shown in FIGS. 8 and 9.

Example 16

Long-Term Cell Culture without Lipofection

The capacity of the anti-HSP27 oligonucleotide having the sequence set forth in SEQ ID NO: 135 to exhibit inhibition of cell proliferation in long-term culture in the absence of lipofection or other transfection agents was investigated. Over twenty cell lines were examined in cell cultures incubated in standard growth media with a range of doses, i.e., 0, 0.32, 0.63, 1.25, 2.5, 5, 10, and 20 micromolar, for the oligonucleotides for a period of 1 to 7 days. Typical media and the cell proliferation assay method are described in Example 9.

In the absence of lipofection, the following cell lines demonstrated no significant inhibition at any oligonucleotide concentration: 15PC3 (a prostate cancer cell line), PC3 (a human prostate cancer cell line), A549 (a human lung cancer cell line), DLD-1 (a human colon cancer cell line), SW480 (a human colon adenocarcinoma cell line), 518A2 (a human melanoma cell line), Calu-6 (a human pulmonary carcinoma cell line), 22RV1 (a human prostate carcinoma cell line), and Hep3B (a human hepatoma cell line). The following cell lines exhibited 20% to 70% inhibition of cell proliferation at 2.5 to 20 micromolar concentrations of SEQ ID NO 135: H1581 (a large cell carcinoma cell line), U87MG (a human glioblastoma-astrocytoma, epithelial-like cell line), A427 (a human lung adenocarcinoma cell line), LNCaP (a human prostate adenocarcinoma cell line), BxPC3 (a human pancreatic cancer cell line), HCC827 (a human esophageal squamous cell carcinoma cell line), DU-145 (a human prostate cancer cell line), H1975 (a non-small cell lung carcinoma cell line), SKBR3 (a human breast carcinoma cell line), Huh7 (a human hepatoma cell line), HT1080 (a human fibrosarcoma cell line), Jimt (a human breast cancer cell line), MB231 (a human breast adenocarcinoma cell line), HCC827R (derived from the lung cancer cell line HCC827), and 786-0 (a human renal cell cancer cell line). Example data after 7 days of cell culture are shown in FIG. 10. Control cell cultures that were not exposed to the oligomer having SEQ ID NO: 135 correspond to 100% cell growth. It is noted that both colon cancer lines tested were unresponsive whereas all three breast cancer cell lines tested were responsive to growth inhibition. Further titration experiments with HT1080 cells and SEQ ID NOs: 135 and 131 demonstrated 1050 values for growth inhibition of 2 micromolar for the oligomers having the sequence set forth in SEQ ID NO: 135 and 0.6 micromolar for SEQ ID NO: 131. In conclusion, the oligomer having the sequence of SEQ ID NO: 135 demonstrated moderate growth inhibition in some, but not all, cell lines under the growth conditions tested.

Example 17

Long-Term Culture with the Oligomer Having the Sequence of SEQ ID NO: 135 Down-Modulates HSP27 mRNA and Protein The biological effects of incubation of antisense oligonucleotides in the cell culture media has been examined. Using higher oligonucleotide concentrations (micromolar) compared to lipofection methods (nanomolar), we evaluated the treatment of cells with these compounds with regard to target down-modulation by measuring the relative levels of the target HSP27 mRNA with standard real-time quantitative polymerase chain reaction methods including measurement of housekeeping genes such as GAPDH to normalize the data. Cell lines were plated in 6-well microwell dishes using the recommended commercial media (ATCC) plus various doses of oligonucleotides. RT-PCR analysis was conducted on an ABI 7500 system and data were analyzed with ABI 7500 Fast System SDS software. Gene-specific probe-primers were designed using ABI software. A PCR example program is as follows: 50° C. for 2 min, 95° C. for 10 min, followed by 40 cycles of 95° C. 15 sec, 60° C. 1 min. The Western blot analysis was analyzed on a Fuji Film LAS-1000 for quantification of chemiluminescence with anti-HSP27 antibody reagents, and anti-tubulin antibodies (R&D Systems). Several cell lines were investigated for the capability of anti-HSP27 oligonucleotides to down-modulate target mRNA and protein levels under conditions of long-term incubation in the absence of lipofection or other transfection agents as described in Example 15. Following 1 to 7 days of cell culture with the oligomer having the sequence of SEQ ID NO: 135 in a 0 to 5 micromolar dosing range, HSP27 mRNA levels were measured by quantitative real-time PCR as described in Example 7. HSP27 protein was measured by Western blot immunoassays using commercial antibody horseradish peroxidase conjugates versus HSP27 or control proteins including alpha-tubulin. Evaluation of the specificity of the down-modulation of HSP27 by the oligomer having the sequence of SEQ ID NO: 135 was performed by assessing the effects of scrambled or mismatched oligonucleotides.

Figure 11A:
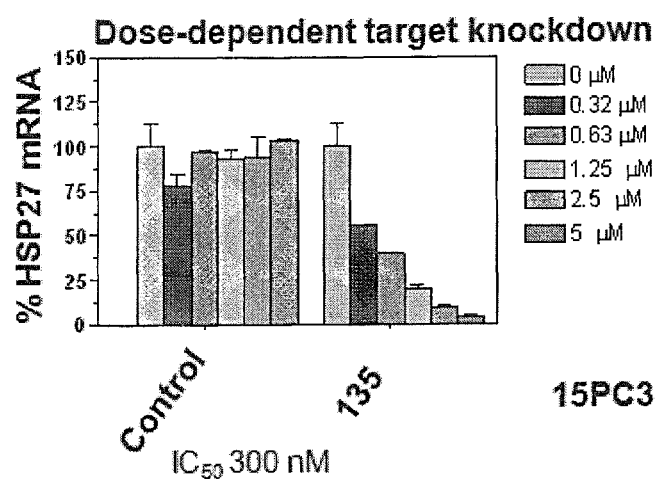
FIGS. 11A and 11B. Long-term culture with the oligomer having the sequence set forth in SEQ ID NO: 135 down-modulates Hsp27 mRNA (FIG. 11A) and protein (FIG. 11B).
Figure 11B:
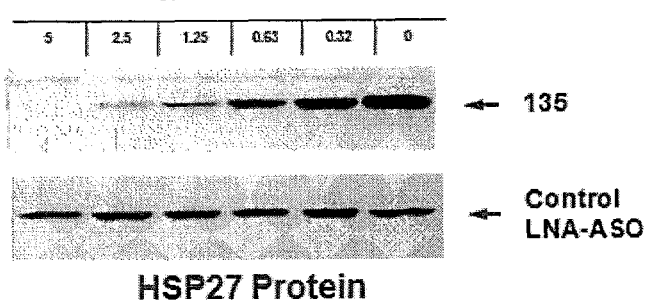

FIG. 11 shows the dose-dependent down-modulation of either HSP27 mRNA (FIG. 11A) or HSP27 protein (FIG. 11B). The approximate IC50 for target down-modulation is 300 nanomolar for HSP27 mRNA or HSP27 protein in the cell line 15PC3 (a prostate cancer cell line) after 6 days. Similar results were obtained for additional cell lines including HT1080 (a human fibrosarcoma cell line), which exhibited a 10-fold knockdown of HSP27 mRNA and HSP27 protein at 2-5 micromolar doses after 3-4 days. The effect on HSP27 mRNA appeared to be specific since an antisense against HERS failed to knock down HSP27 mRNA. In conclusion, incubation of LNA-based antisense oligonucleotides in cell cultures of tumor cell lines, can exhibit a dose-dependent and sequence-specific reduction in the levels of the target HSP27 mRNA and protein.

Example 18

Combination Effects of Anti-HSP27 LNA-Based Oligonucleotides Plus TNFα on Cellular Growth Several cell lines were investigated for the capability of anti-HSP27 oligonucleotides to inhibit cell growth when combined with another cytotoxic agent under conditions of long-term incubation in the absence of lipofection or other transfection agents.

Figure 12:
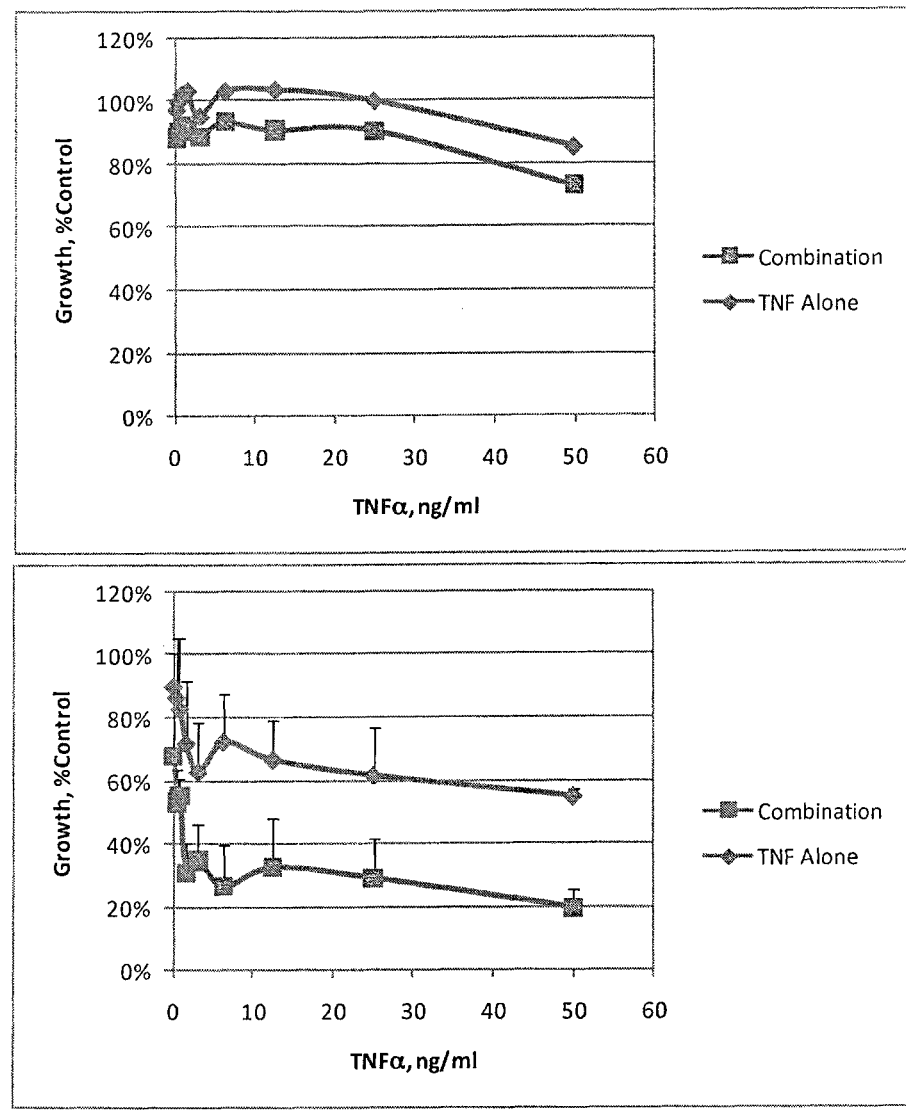
FIG. 12. Example of combination effects of anti-Hsp27 LNA-based oligonucleotide plus cytotoxic agent: Effect of combination with TNF· on cellular growth.

Long-term culture of 15PC3 cells (prostate cancer cell line) with 10 micromolar of the oligomer having the sequence of SEQ ID NO: 135 for 5 days followed by 3 days of incubation with a dose range (0-50 ng/mL) of TNF-alpha resulted in additive effects of the two agents (FIG. 12, top). Long-term culture of BxPC3 cells (a human pancreatic cancer cell line) with 10 micromolar of the oligomer having the sequence of SEQ ID NO: 135 for 5 days followed by 3 days of incubation with a dose range of TNF-alpha resulted in additive, or more than additive, effects on cell proliferation (FIG. 12, bottom). Similar results were obtained when cells were treated with TNF· and the oligomer having the sequence of SEQ ID NO:

135 simultaneously for 7 days. HSP27 is reported to participate in the death receptor signaling pathways and these results support the proposed role of HSP27 in modulating this pathway.

Hence, anti-HSP27 oligonucleotides may be used therapeutically in combination with a variety of conventional cytotoxics—examples are TRAIL, 5-fluoruracil, vincristine, doxorubicin, and camptothecin. Other combinations may include use of anti-HSP27 oligonucleotides as a radiation sensitizer, or in combination with various anticancer antibodies or small molecules, particularly where resistance to these agents has occurred. In conclusion, the chaperone functions of HSP27 may play a role in resistance to the cytotoxic activity of many therapies and HSP27 antisense molecules may provide beneficial counteracting activity to enhance the overall therapeutic efficacy of the combination of these agents.

Example 19

Anti-Tumor Effects of Anti-HSP27 Oligonucleotides in Animal Models

Figure 13:
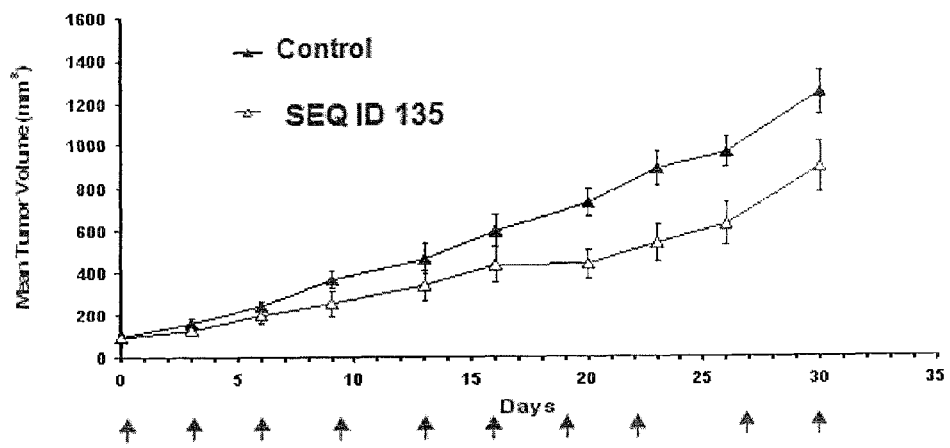
FIG. 13. Anti-tumor effects of the oligomer having the sequence set forth in SEQ ID NO: 135 in PC3 Xenograft.

Two human tumor models, PC3 (a human prostate cancer cell line) and DU-145 (a human prostate cancer cell line), were investigated for the capability of anti-HSP27 oligonucleotides to demonstrate tumor growth inhibition (TGI) in xenograft studies in mice. In the first study, subcutaneous tumors of PC3 were established in athymic nude mice and after tumor volume reached approximately 100 mm$^3$, the mice were administered either 3, 10, 30, or 100 mg/kg intravenous doses of one of five oligonucleotides, SEQ ID. NOs: 129, 130, 131, 132, and 135. The dosing regimen was every third day for four total doses. Antitumor effects were observed in SEQ ID NOs: 130, 131, and 135, with tumor growth inhibition at day 10, based on mean tumor volumes (5 mice per group), exhibiting 26%-66% TGI. A second study with PC3 or DU-145 tumor xenografts in mice was conducted using 3 mg/kg of SEQ ID NO: 135 every third day for a total of ten doses. A 30% TGI was observed in both PC3 and DU-145 models at this dose at day 29 (FIG. 13). A third study examined the TGI effects of SEQ ID NO: 135 in the PC3 xenograft model at an i.v. dose of 60 mg/kg every third day for ten doses. A 40% TGI was observed at day 29 based on mean tumor volume (6 mice per group) which did not however achieve statistical significance in this study.

Example 20

Target Knockdown in Tumors by Anti-HSP27 Oligonucleotides in Animal Models

The human tumor model PC3 (a human prostate cancer cell line) was investigated for the capability of anti-HSP27 oligonucleotides to demonstrate target mRNA and protein knockdown in xenograft studies in mice. In this study, subcutaneous tumors of PC3 were established in athymic nude mice and after tumor volume reached approximately 100 mm$^3$, the mice were administered either 3, 10, 30, or 100 mg/kg intravenous doses of one of five oligonucleotides having the sequence set forth in SEQ ID NO: 129, 130, 131, 132, and 135 (data not shown for the oligomers having the sequences set forth in SEQ ID NOs: 129, 130 and 132). The dosing regimen was every third day for four total doses. Tumor tissues from these studies were collected either into RNAlater for mRNA analysis or flash-frozen for protein analysis. PC3 tumor sections were processed 24 hr after the final dose of oligonucleotide. Quantitative real-time PCR was conducted as described in Example 14 and protein quantitation by immunoassays was performed as described in Example 17.

Figure 14:
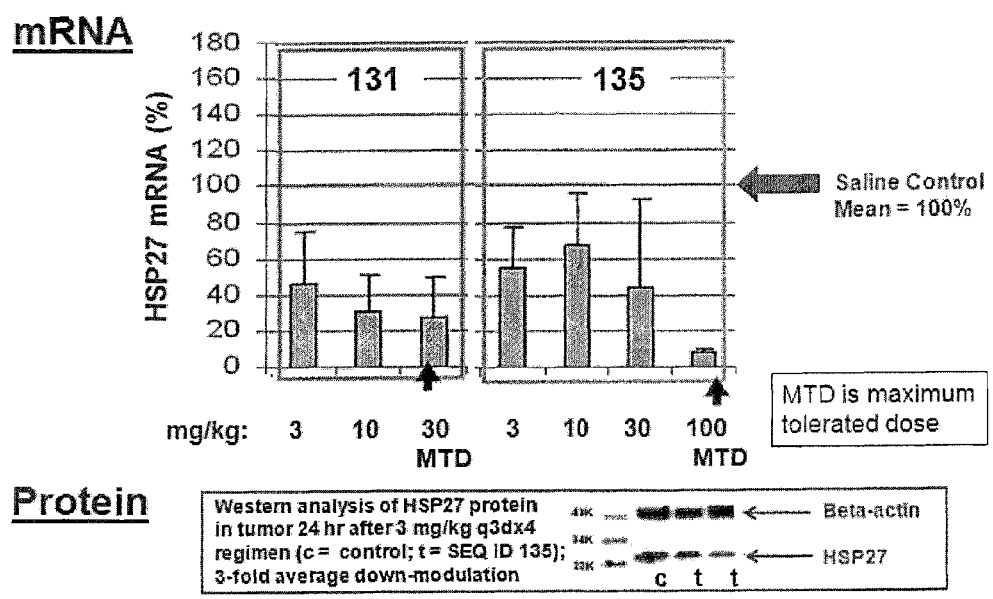
FIG. 14. Target Knockdown in Tumors by anti-Hsp27 Oligonucleotides in Animal Models. The size of the bands in the marker are 43 KDa, 34 KDa and 23 KDa.

HSP27 mRNA in tumor tissue was down-modulated by the oligomers having the sequences set forth in SEQ ID NO: 131 and SEQ ID NO: 135 at the maximum tolerated dose (MTD) for each compound, either 30 mg/kg or 100 mg/kg for the oligomer having the sequences of SEQ ID NO: 131 and SEQ ID NO: 135, respectively (see FIG. 14). HSP27 protein down-modulation was also observed for both oligomers (having the sequences set forth in SEQ ID NO: 131 and SEQ ID NO: 135) with the average HSP27 protein knockdown in multiple tumor samples of approximately 3-fold reduction. The mRNA knockdown with the oligomer having the sequence of SEQ ID NO: 135 was approximately 10-fold at the MTD. In conclusion, LNA-based antisense oligonucleotides versus HSP27 demonstrated target-specific mRNA and protein down-modulation in tumor tissues in this dosing regimen.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

The invention claimed is:

1. An oligomer consisting of 16 monomers and having the nucleobase sequence of SEQ ID NO:91.

2. The oligomer of claim 1, wherein at least one of the monomers is a nucleoside analogue.

3. The oligomer of claim 2, wherein the nucleoside analogue is a locked nucleic acid (LNA).

4. The oligomer of claim 3, wherein the LNA is Beta-D-oxy-LNA.

5. The oligomer of claim 3, wherein 4-8 of the 16 monomers are LNA.

6. The oligomer of claim 5, wherein the oligomer is a gapmer.

7. The oligomer of claim 6 wherein the oligomer includes at least one phosphorothioate linkage between monomers.

8. The oligomer of claim 6 wherein the oligomer is SEQ ID NO:135.

9. A conjugate comprising the oligomer according to claim 1 and at least one non-nucleotide or non-polynucleotide moiety covalently attached to the oligomer, wherein the conjugate comprises no more than 16 monomers.

10. A pharmaceutical composition comprising the oligomer according to claim 1, or a conjugate comprising the oligomer of claim 1 and at least one non-nucleotide or non-polynucleotide moiety covalently attached to the oligomer, and a pharmaceutically acceptable diluent, carrier, salt or adjuvant, wherein the conjugate comprises no more than 16 monomers.

11. A method for treating prostate cancer comprising administering the oligomer according to claim 1, or a conjugate comprising the oligomer of claim 1 and at least one non-nucleotide or non-polynucleotide moiety covalently attached to the oligomer to a patient in need thereof, wherein the conjugate comprises no more than 16 monomers.

12. The method of claim 11 further comprising treating the prostate cancer with radiation therapy.

* * * * *